United States Patent [19]
Larsen et al.

[11] Patent Number: 5,916,560
[45] Date of Patent: Jun. 29, 1999

[54] METHODS FOR INHIBITING AN IMMUNE RESPONSE BY BLOCKING THE GP39/CD40 AND CTLA4/CD28/B7 PATHWAYS AND COMPOSITIONS FOR USE THEREWITH

[75] Inventors: Christian P. Larsen, Atlanta, Ga.; Alejandro A. Aruffo, Edmonds, Wash.; Diane L. Hollenbaugh, Seattle, Wash.; Peter S. Linsley, Seattle, Wash.; Jeffrey A. Ledbetter, Seattle, Wash.; Thomas C. Pearson, Atlanta, Ga.

[73] Assignees: Bristol-Myers Squibb Company, Pinceton, N.J.; Emory University, Atlanta, Ga.

[21] Appl. No.: 08/821,400

[22] Filed: Mar. 20, 1997

Related U.S. Application Data

[60] Provisional application No. 60/013,751, Mar. 20, 1996.
[51] Int. Cl.$^6$ .................................................. C07K 16/28
[52] U.S. Cl. ..................................... 424/154.1; 424/130.1; 424/139.1; 424/143.1; 424/153.1; 424/173.1; 514/2; 514/8; 530/387.3; 530/388.73; 530/388.75
[58] Field of Search ............................. 424/131.1, 135.1, 424/139.1, 143.1, 184.1, 154.1, 130.1, 153.1, 173.1; 530/387.1, 387.3, 388.73, 388.75; 514/2, 8

[56] References Cited

U.S. PATENT DOCUMENTS

| | | | |
|---|---|---|---|
| 5,434,131 | 7/1995 | Linsley et al. | 514/2 |
| 5,474,771 | 12/1995 | Lederman et al. | 424/133.1 |
| 5,652,224 | 7/1997 | Wilson | 514/44 |
| 5,677,165 | 10/1997 | de Boeli | 435/240.27 |
| 5,683,693 | 11/1997 | Noelle | 424/144.1 |
| 5,698,679 | 12/1997 | Nemazee | 530/387.3 |
| 5,747,037 | 5/1998 | Noelle | 424/154.1 |

FOREIGN PATENT DOCUMENTS

| | | |
|---|---|---|
| 0 555 880 A2 | 8/1993 | European Pat. Off. |
| WO 92/00092 | 1/1992 | WIPO |
| WO 94/01547 | 1/1994 | WIPO |

OTHER PUBLICATIONS

Kennedy, Eur J. Immunol, 24, 116, 1994.
N. Griggs et al., 1995, Contribution of CD28/CTLA4/B7 and gp39/CD40 . . . , J. Cell Biochem, Suppl. 21A:141 (Exhibit 4).
E. Elwood et al., 1996, Long–term murine skin allograft survival . . . , Surgical Forum, 47:427 (Exhibit 5).
M. Schaub et al., 1997, Synergistic effect of CD40L/CD40 and CD28 . . . , J. Aller. and Clin. Immunol. 991(2):S206 (Exhibit 6).
A. Tang et al., 1996, Suppression of murine allergic contact dermatitis by CTLA41g, J. Immunol., 157(1):117 (Exhibit 7).
Linsley et al. (1991) J. Exp. Med. 173:721–730 (Exhibit 1).
Freireich et al. (1966) Cancer Chemotheraphy Reports 50(4):219–244 (Exhibit 2).
Yokochi et al. (1982) J. of Immunol. 128:823–827 (Exhibit 3).
Linsley et al. (1990) Proc. Natl. Acad. Sci. 87:5031–5035 (Exhibit 4).
Lenschow et al. (1992) Science 257:789–792 (Exhibit 5).
June et al. (1990) Immunol. Today 11(6):211–216 (Exhibit 6).
van Essen, D. et al. (1995) Nature 378:620–623 (Exhibit 9).
Foy, T.M. et al. (1993) J. Exp. Med. 178:1567–75 (Exhibit 10).
Boussiotis, V.A. et al. (1993) J. Exp. Med. 178:1753–1763 (Exhibit 11).
Parker et al. (1995) Proc. Natl. Acad. Sci. USA 92:9560–9564 (Exhibit 12).
Damle et al. (1981) Proc. Natl. Acad. Sci. 78:5096–5098 (Exhibit 13).
Durie, F.H. et al. (1993) Science 261:1328–30 (Exhibit 14).
Qin et al. (1993) Science 259:974–977 (Exhibit 15).
Platt, J.L. (1996) Curr. Opin. Imm. 8:721–728 (Exhibit 16).
Schwartz, R.H. (1992) Cell 71:1065–8 (Exhibit 17).
Sharabi et al. (1990) J. Exp. Med. 172:195–202 (Exhibit 18).
Mayumi, H. & Good, R.A. (1990) J. Exp. Med. 169:213–238 (Exhibit 19).
Qin et al. (1989) J. Exp. Med. 169:779–794 (Exhibit 20).
Pierson III et al. (1989) J. Exp. Med. 170:991–996 (Exhibit 21).
Alderson et al. (1993) J. Exp. Med. 178:669–674 (Exhibit 22).
Hollenbaugh, D. et al. (1995) J. Exp. Med. 182:33–40 (Exhibit 23).
Van den Eertwegh, A.J.M. et al. (1993) J. Exp. Med. 178:1555–65 (Exhibit 24).
Ilstad et al. (1985) J. Exp. Med. 162:231–44 (Exhibit 25).
Noelle R. et al. (1992) Proc. Natl. Acad. Sci. 89:6550–6554 (Exhibit 26).
Freedman et al. (1987) J. Immunol. 139:3260–3267 (Exhibit 27).
Freeman et al. (1989) J. Immunol. 143(8):2714–2722 (Exhibit 28).
Turka et al. (1992) Proc. Natl. Acad. Sci. USA 89:11102–11105 (Exhibit 29).
Corry et al. (1973) Transplantation 16(4):343–350 (Exhibit 30).

(List continued on next page.)

*Primary Examiner*—Cecilia J. Tsang
*Assistant Examiner*—David Lukton
*Attorney, Agent, or Firm*—Mandel & Adriano

[57] ABSTRACT

The present invention provides a method for inhibiting an immune reponse and a method for inhibiting rejection of transplanted tissues. This method comprises preventing an endogenous molecule on a cell selected from the group consisting of gp39 and CD40 antigens from binding its endogenous ligand and preventing an endogenous molecule on a cell selected from the group consisting of CTLA4, CD28, and B7 antigens from binding its endogenous ligand. The prevention of such molecules from binding their ligand thereby blocks two independent signal pathways and inhibits the immune response resulting in transplanted tissue rejection.

24 Claims, 22 Drawing Sheets

OTHER PUBLICATIONS

Aksentijevich et al. (1992) Transplantation 53(5):1108–14 (Exhibit 31).
Jenkins, M.K. et al. (1991) J. Immunol. 147:2461–6 (Exhibit 32).
Malyguine, A.M. (1996) Transplantation 61(1):161–164 (Exhibit 33).
Banchereau, J. et al. (1994) Ann. Rev. Immunol. 12:881–992 (Exhibit 34).
Larson et al. (1994) J. Immunol. 152:5208–5219 (Exhibit 35).
Cayabyab et al. (1994) J. Immunol. 152:1523–31 (Exhibit 36).
Clark et al. (1986) Human Immunol. 16:100–113 (Exhibit 37).
Cotterell et al. (1995) Transplantation 60(8):861–868 (Exhibit 38).
Larson et al. (1996) Transplantation 61:4–9 (Exhibit 39).
Bluestone, J.A. (1995) Immunity 2:555–9 (Exhibit 40).
Zhao et al. (1996) Nat. Med. 2(11):1211–1216 (Exhibit 41).
Cobbold et al. (1986) Nature 323:164–166 (Exhibit 42).
Larsen et al. (1996) Nature 381:434–438 (Exhibit 43).
Armitage, R.J. et al. (1992) Nature 357:80–2 (Exhibit 44).
Grewal, I.S. et al. (1995) Nature 378:617–620 (Exhibit 45).
Ildstad, S.T., Sachs, D.H. (1984) Nature 307:168–170 (Exhibit 46).
Pereira et al. (1990) J. Immunol. 144:2109–2116 (Exhibit 47).
Ochs et al. (1994) Research in Immunology 145(3):210–215; discussion 244–9 (Exhibit 48).
Ochs et al. (1994) Semin. Immunol. 6(5):337–41 (Exhibit 49).
Durie et al. (1994) J. Clin. Invest. 94(3):1333–8 (Exhibit 50).
Lu et al. (1996) J. Immunol. 156(9):3327–33 (Exhibit 51).
Malik, N. (1996) J. Immunol. 156(10):3952–60 (Exhibit 52).
Kiener et al. (1995) J. Immunol. 155(10):4917–25 (Exhibit 53).
Hollenbaugh et al. (1995) J. Immunol. Methods 188(1):1–7 (Exhibit 54).
Durie et al. (1994) Res. Immunol. 145(3):200–5; discussion 244–9 (Exhibit 55).
Noelle, R.J. (1995) Clin. Immunol. Immunopathol. 76(3 Pt 2):S203–7 (Exhibit 56).
Griggs et al. (1996) J. Exp. Med. 183(3):801–810 (Exhibit 57).
Foy et al. (1995) J. Exp. Med. 182(5):1377–88 (Exhibit 58).
Foy et al. (1994) J. Exp. Med. 180(1):157–63 (Exhibit 59).
Green et al. (1996) J. Virol. 70(4):2569–75 (Exhibit 60).
Farrington et al. (1994) Proc. Natl. Acad. Sci. USA 91(3):1099–103 (Exhibit 61).
Foy et al. (1994) Semin. Immunol. 6(5):259–66 (Exhibit 62).
Gilliland et al. (1996) Tissue Antigens 47(1):1–20 (Exhibit 63).
Resetkova et al. (1996) Thyroid 6(4):267–73 (Exhibit 64).
Durie et al. (1994) Immunol. Today 15(9):406–11 (Exhibit 65).
Buhlamnn, J.E., Noelle, R.J. (1996) J. Clin. Immunol. 16(2)83–9 (Exhibit 66).
Foy et al. (1996) Annu. Rev. Immunol. 14:591–617 (Exhibit 67).
Ledbetter et al. (1994) Circulatory Shock 44(2):67–72 (Exhibit 68).
Laman et al. (1996) Crit. Rev. Immunol. 16(1):59–108 (Exhibit 69).
Bajorath et al. (1995) Biochemistry 34(6):1833–44 (Exhibit 70).
Bajorath et al. (1995) Biochemistry 34(31):9884–92 (Exhibit 71).
Denfeld et al. (1996) Eur. J. Immunol. 26(10):2329–34 (Exhibit 72).
Roy et al. (1995) Eur. J. Immunol. 25(2):596–603 (Exhibit 73).
Gerritse et al. (1996) Proc. Natl. Acad. Sci. USA 93(6):2499–504 (Exhibit 74).

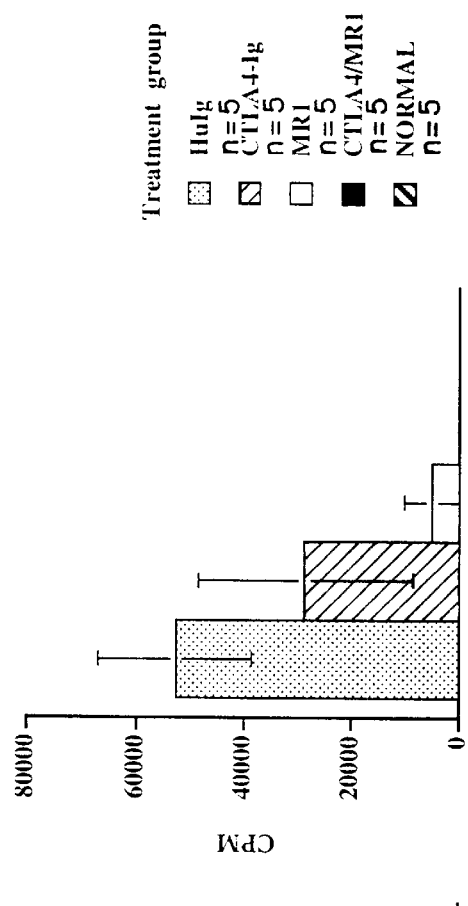
FIG. 6A weight ratios
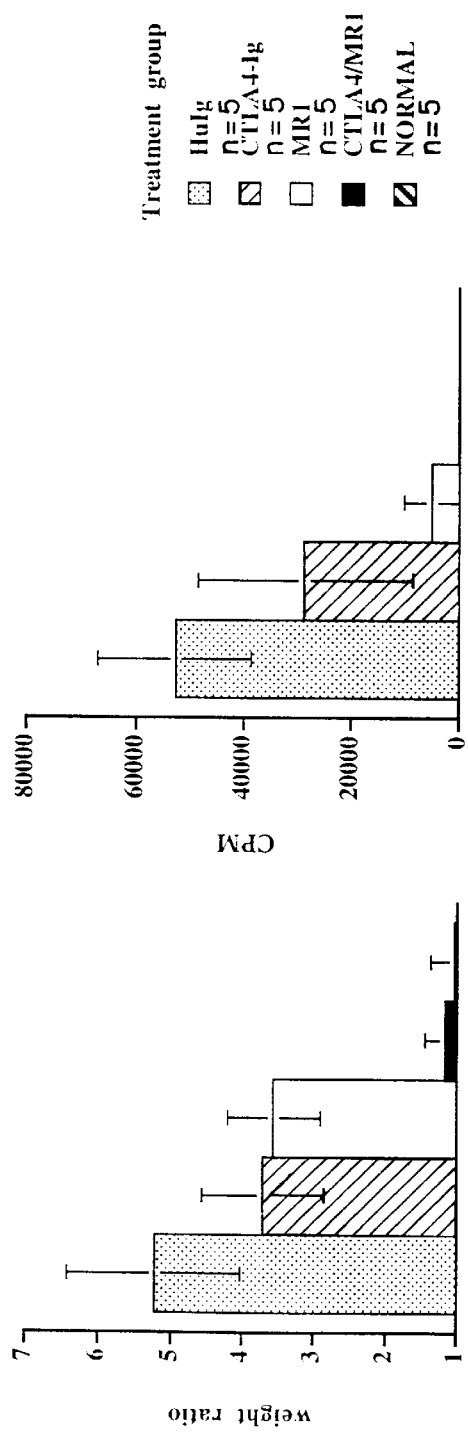
FIG. 6B H³ proliferation
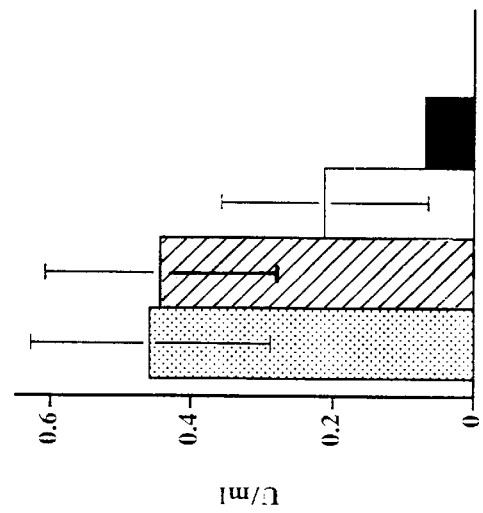
FIG. 6C IFNγ production
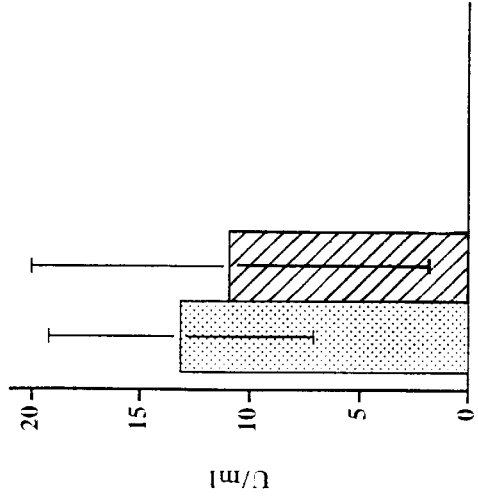
FIG. 6D IL2 production 5,916,560

METHODS FOR INHIBITING AN IMMUNE RESPONSE BY BLOCKING THE GP39/CD40 AND CTLA4/CD28/B7 PATHWAYS AND COMPOSITIONS FOR USE THEREWITH

This application is based on United States provisional patent application Ser. No. 60/013,751 filed on Mar. 20, 1996.

Throughout this application various publications are referenced. The disclosures of these publications in their entireties are hereby incorporated by reference into this application in order to more fully describe the state of the art to which this invention pertains.

BACKGROUND OF THE INVENTION

CD28 is expressed on most T lineage cells and plasma cells (June, C. H. et al., Immunol. Today 11, 211–16 (1990); Damle et al., Proc. Natl. Acad. Sci. 78:5096–6001 (1981)). The ligand for CD28 is B7, which is expressed on activated B cells (Linsley, P. S. et al., Proc. Natl. Acad. Sci. USA 87, 5031–35 (1990); Linsley, P. S. et al., J. Exp. Med. 173, 721–730 (1991).

CD40 is a member of the tumor necrosis factor receptor (TNFR) family of type I membrane-bound signaling receptors. Though originally identified as a B cell antigen, CD40 is expressed by all antigen presenting cells (APC) including dendritic cells, monocytes, and B cells.

The ligand for CD40 is gp39, which binds to CD40 and thus can activate B cells. Gp39 is also known as CD40L, TRAP and T-BAM. Gp39 is a type II cell surface protein with significant homology to TNF and is transiently expressed by activated T cells. In addition to T cells, gp39 is expressed by basophils, mast cells, and eosinophils.

The CD28 and CD40 pathways play essential roles in the initiation and amplification of T-dependent immune responses (Bluestone, J. A. Immunity 2, 555–9 (1995); Banchereau J., et al. Ann. Rev. Immunol. 12, 881–922 (1994); Durie, F. H., et al. Science 261, 1328–30 (1993); Foy, T. M., et al. J Exp Med 178, 1567–75 (1993); Van den Eertwegh, A. J. M., et al. J Exp Med 178, 1555–65 (1993)).

CD28/B7 interactions provide critical "second signals" necessary for optimal T cell activation, and IL-2 production (Jenkins, M. K., et al. J. Immunol. 147, 2461–6 (1991); Schwartz, R. H. Cell 71, 1065–8 (1992); Boussiotis, V. A., et al. J. Exp. Med. 178, 1753–1763 (1993)), whereas CD40/gp39 signals provide costimulation for B cell, macrophage, endothelial cell, and T cell activation (Grewal, I. S., et al. Nature 378, 617–620 (1995); van Essen, D., et al. Nature 378, 620–623 (1995); Hollenbaugh, D., et al. J. Exp. Med. 182, 33–40 (1995); Armitage, R. J., et al. Nature 357, 80–2 (1992); Cayabyab, M., et al. J. Immunol. 152, 1523–31 (1994); Noelle, R., et al. Proc. Natl. Acad. Sci. USA 89, 6550–6554 (1992); Alderson, M. et al. J. Exp. Med. 178, 669–674 (1993)).

Host immune responses often cause rejection of transplanted tissues and organs. Thus, inhibition of those immune responses are critical in the success of tissue transplantation. There have been studies aimed at blocking either of the CD28 or CD40 pathways, however, blockade of either of these pathways alone has not been sufficient to permit engraftment of highly immunogenic allografts (Turka, L. A., et al. Proc. Nat'l Acad. Sci. USA 89, 11102–11105 (1992); Parker, D. C., et al. Proc. Nat'l Acad. Sci. USA 92, 9560–9564 (1995); Larsen, C. P. et al. Transplantation 61, 4–9 (1996)). The monotherapies blocking either CD28 or CD40 pathway only resulted in at best temporary, and sometimes longer, periods of survival of transplanted tissues. Neither blockade alone uniformly promoted graft survival.

The vigorous immune response to xenogeneic organ transplants has served as a powerful barrier to the application of this technique to clinical transplantation (Platt J. L., Curr. Opin. Imm. 8, 721–728 (1996). Previous experimental attempts to prolong xenogeneic skin grafts have required either whole body irradiation followed by mixed xeno/syngeneic reconstitution (Ildstad S. T., Sachs D. H., Nature, 307: 168–170 (1984)), or rigorous preconditioning with thymectomy combined with depleting anti-T cell antibodies (Pierson III R. N., Winn H. J., Russell P. S., Auchincloss Jr. H., J. Exp. Med., 170:991–996 (1989); and Sharabi Y, Aksentijevich I., Sundt III T. M., Sachs D. H., Sykes M., J. Exp. Med., 172:195–202 (1990). These strategies have recently been used to promote skin graft acceptance across a discordant xenogeneic barrier (Zhao Y., Swenson K., Sergio J., Arn J. S., Sachs D. H., Sykes M., Nat. Med., 2(11):1211–1216 (1996)). However, the potential morbidity associated with cytoablative treatment regimens present a significant obstacle to the introduction of these strategies into use in clinical solid organ transplantation. Thus the development of non-cytoablative strategies to prolong xenograft survival would greatly facilitate the clinical application of these techniques.

Presently, there exists a need to provide ways to effect long-term tolerance of transplanted tissues by the host, thereby increasing the survival rate of transplantation. To do so, it is necessary to ensure sufficient immunologic unresponsiveness in the transplant recipient.

We have found that the inhibition of T-dependent immune responses resulting from blockade of either CD28 or CD40 signals is potent, but incomplete. The data herein demonstrate that simultaneous blockade of these pathways unexpectedly inhibits acute and chronic rejection of transplanted tissue in vivo. Independent blockade of these pathways using a soluble CTLA4 molecule or antibodies which recognize and bind gp39 failed to even minimally prolong survival of primary skin transplanted tissue.

The invention herein involves the discovery that simultaneous blockade of CD28 and CD40 signals promoted long-term survival of fully allogeneic as well as xenogeneic skin grafts. Prolongation of skin allograft survival was eliminated by cyclosporine A (CyA), suggesting that it is an active process requiring intact signaling via the TcR/CD3 complex and/or other CyA sensitive pathways. Moreover, CTLA4Ig/MR1 promoted long-term acceptance of primarily vascularized cardiac graft tissue, and inhibited the development of chronic vascular rejection.

The effect demonstrated in the two transplantation models herein indicates that CD28 and CD40 provide interrelated, yet independent signaling pathways required for the generation of effective T cell responses. This discovery provides methods which are new and more effective strategies to manipulate immune responses including suppressing graft rejection.

SUMMARY OF THE INVENTION

The present invention provides a method for inhibiting rejection of a transplanted tissue. This method comprises preventing an endogenous molecule (e.g., antigen) on a cell selected from the group consisting of gp39 and CD40 from binding its endogenous ligand and preventing an endogenous molecule on a cell selected from the group consisting of CTLA4, CD28, and B7 from binding its endogenous ligand. The prevention of such molecules from binding their ligands thereby blocks two independent signal pathways and inhibits the immune response responsible for transplanted tissue rejection.

Further, the invention provides a method for inhibiting an immune response involved with transplanted tissue rejection comprising contacting a B7-positive cell with a first soluble ligand which recognizes and binds the B7 antigen, and contacting a gp39-positive cell with a second soluble ligand which recognizes and binds the gp39 antigen. The binding of the B7-positive cell to the first soluble ligand blocks the reaction of the B7 antigen with endogenous CTLA4 or CD28. Additionally, the binding of the gp39 antigen to the second soluble ligand blocks the reaction of gp39 antigen with endogenous CD40. This blockage of both the gp39 and B7 pathways inhibits immune responses.

Applicants' discovery includes a method for inhibiting immune responses mediated by the gp39 and B7 pathways in a subject. This method comprises administering to the subject a first soluble ligand which recognizes and binds the B7 antigen and a second soluble ligand which recognizes and binds the gp39 antigen.

The binding of both the first and second soluble ligands to their receptors inhibits the immune response mediated by the gp39 and B7 pathways by preventing an endogenous molecule on a cell selected from the group consisting of gp39 and CD40 antigens from binding its endogenous ligand and preventing an endogenous molecule on a cell selected from the group consisting of CTLA4, CD28, or B7 from binding its ligand.

The present invention also provides a method for inhibiting transplant rejection in a subject. This method comprises administering to the subject an effective amount of a combination of a first soluble ligand which recognizes and binds the B7 antigen on B7-positive cells and a second soluble ligand which recognizes and binds the gp39 antigen on gp39-positive cells.

The binding of B7-positive cells with the first soluble ligand and gp39-positive cells with the second soluble ligand disrupts endogenous CTLA4-, CD28-, and gp39-positive cell interactions with B7-positive cells and gp39-positive cells so that transplant rejection is inhibited.

BRIEF DESCRIPTION OF THE FIGURES

FIG. 6A is a bar graph showing weight of the immunized popliteal lymph node relative to the contralateral node in C3H mice in response to foot pad immunization with irradiated (2000 RADS) rat (Sprague-Dawley) splenocytes. Human IgG (stippled), CTLA4-Ig (gray), MR1 (white), CTLA4Ig/MR1 (black), normal unimmunized node (hatched).

FIG. 6B is a line graph showing in vitro proliferation of lymph node cells after harvesting the popliteal lymph at five days after immunization. Human IgG (stippled), CTLA4Ig (gray), MR1 (white), CTLA4-Ig/MR1 (black), normal unimmunized node (hatched).

FIG. 6C is a bar graph showing that simultaneous blockade of the CD40 and CD28 pathways markedly inhibits cytokine production of IL-2. Human IgG (stippled), CTLA4-Ig (gray), MR1 (white), CTLA4-Ig/MR1 (black), normal unimmunized node (hatched).

FIG. 6D is a bar graph showing that simultaneous blockade of the CD40 and CD28 pathways markedly inhibits cytokine production of INFγ. Human IgG (stippled), CTLA4-Ig (gray), MR1 (white), CTLA4-Ig/MR1 (black), normal unimmunized node (hatched).

DETAILED DESCRIPTION OF THE INVENTION

Definitions

Figure 1:
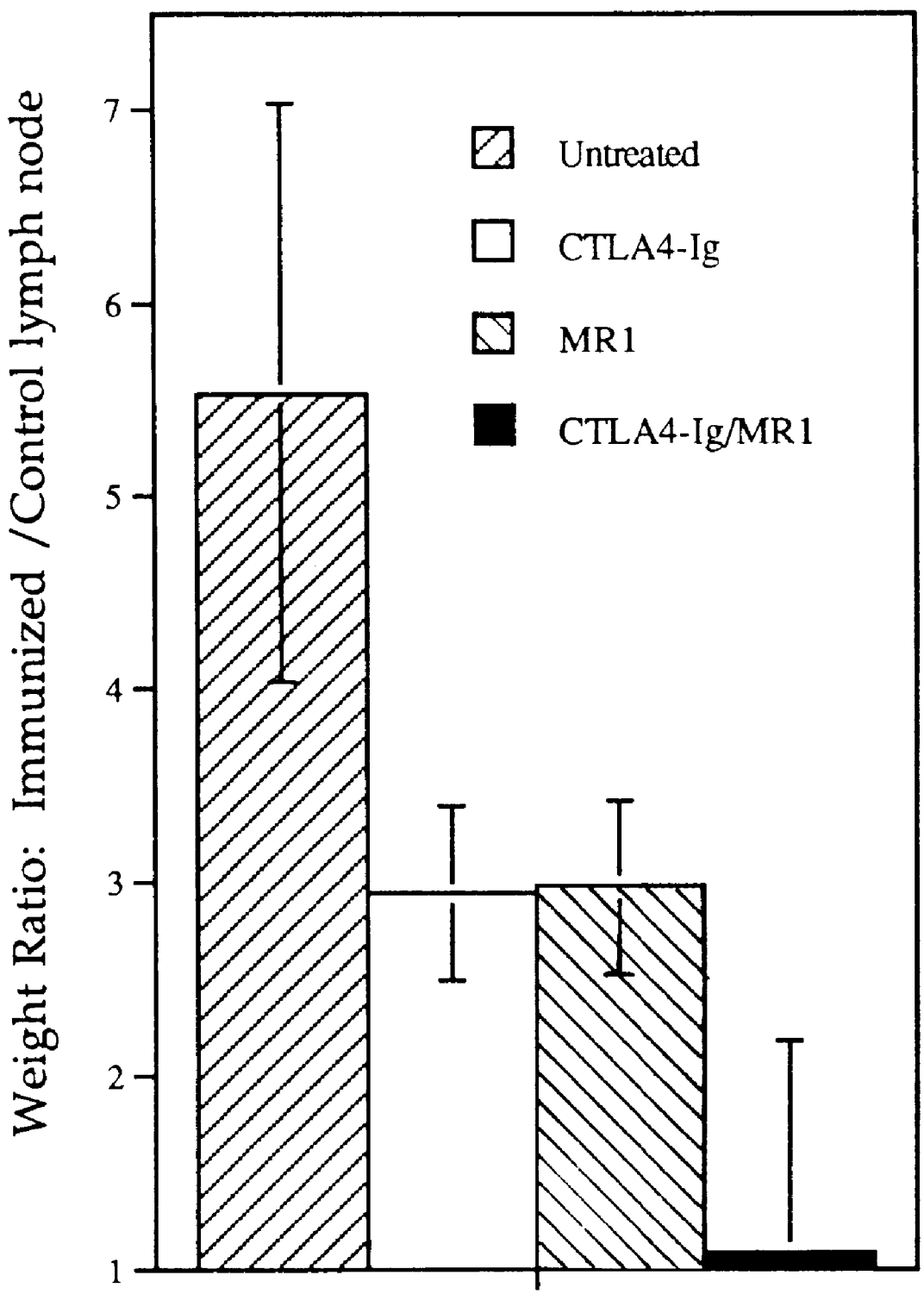
FIG. 1 is a bar graph showing that simultaneous blockade of CD28 and CD40 signals ablate popliteal lymph node alloimmune responses in vivo.

All scientific and technical terms used in this application have meanings commonly used in the art unless otherwise specified. As used in this application, the following words or phrases have the meanings specified.

As used herein "monoclonal antibodies directed against gp39" or "anti-gp39" includes MR1. Anti-gp39 is also known in the literature as an antiCD40 ligand. Examples of MR1 include, but are not limited to monoclonal antibodies directed against gp39 from mouse; antibodies directed against gp39 from other species such as monkey, sheep, human are included. Additionally, "monoclonal antibodies directed against gp39" or "anti-gp39" includes any antibody molecule, fragment thereof, or recombinant binding protein that recognizes and binds gp39.

As used herein, "administering" means oral administration, administration as a suppository, topical contact, intravenous, intraperitoneal, intramuscular or subcutaneous administration, or the implantation of a slow-release device such as a miniosmotic pump, to the subject.

As used herein, "pharmaceutically acceptable carrier" includes any material which when combined with the antibody retains the antibody's immunogenicity and is non-reactive with the subject's immune systems. Examples include, but are not limited to, any of the standard pharmaceutical carriers such as a phosphate buffered saline solution, water, emulsions such as oil/water emulsion, and various types of wetting agents. Other carriers may also include sterile solutions, tablets including coated tablets and capsules.

Typically such carriers contain excipients such as starch, milk, sugar, certain types of clay, gelatin, stearic acid or salts thereof, magnesium or calcium stearate, talc, vegetable fats or oils, gums, glycols, or other known excipients. Such carriers may also include flavor and color additives or other ingredients. Compositions comprising such carriers are formulated by well known conventional methods.

As used herein, "transplanted tissue" includes autografts, isografts, allografts, and xenografts. Examples of transplanted tissue include, but are not limited to, solid organ transplants such as heart, liver or kidney, skin grafts, pancreatic islet cells, bone marrow grafts or cell suspensions.

As used herein, "B7" includes B7-1 (also called CD80), B7-2 (also called CD86), B7-3, and the B7 family, e.g., a combination of B7-1, B7-2 and/or B7-3.

In order that the invention herein described may be more fully understood, the following description is set forth.

The discovery herein is related to a method for inhibiting rejection of a transplanted tissue. In one embodiment, the method comprises preventing an endogenous molecule on a cell selected from the group consisting of gp39 and CD40 from binding its endogenous ligand. The method provides preventing an endogenous molecule on a cell selected from the group consisting of CTLA4, CD28, and B7 from binding its endogenous ligand. The prevention of these molecules from binding their endogenous ligands blocks two independent signal pathways. The blockage of these two independent signal pathways inhibits the immune responses that cause transplanted tissue rejection.

In one example of the invention, endogenous gp39 antigen is prevented from binding its endogenous ligand. This example comprises the step of contacting a gp39-positive cell with a soluble ligand which recognizes and binds the gp39 antigen (e.g., by using soluble ligands such as MR1 or other antibodies which bind gp39, and soluble CD40 molecules).

This example comprises the additional step of preventing the endogenous CTLA4 antigen from binding its endogenous ligand. This comprises the step of contacting a B7-positive cell with a soluble ligand which recognizes and binds the B7 antigen such as CTLA4Ig (U.S. Pat. No. 5,434,131, issued Jul. 18, 1995), the BB-1 monoclonal antibody or other antibodies directed against B7.

The binding of the gp39-positive cell to its soluble ligand blocks the reaction of endogenous gp39 antigen with endogenous CD40. The binding of the B7-positive cell to its soluble ligand blocks the reaction of the endogenous B7 antigen with endogenous CTLA4 and CD28. This combined blockage inhibits the immune response.

In another example, endogenous CD40 antigen is prevented from binding its endogenous ligand. This example comprises the step of contacting a CD40-positive cell with a soluble ligand which recognizes and binds the CD40 antigen. Suitable ligands include antibodies directed against CD40 or soluble gp39 (sgp39).

This example comprises the additional step of preventing the endogenous CTLA4 antigen from binding its endogenous ligand. This step comprises contacting a B7-positive cell with a soluble ligand which recognizes and binds the B7 antigen. Examples of this soluble ligand include CTLA4Ig, soluble CD28 molecules, and antibodies directed against B7.

The binding of the CD40-positive cell to its soluble ligand blocks the reaction of endogenous CD40 antigen with endogenous gp39. The binding of the B7-positive cell to its soluble ligand blocks the reaction of the B7 antigen with endogenous CTLA4. The combined blockage inhibits the immune response.

In yet another example, endogenous gp39 antigen is prevented from binding its endogenous ligand as described above. The example comprises the additional step of preventing the endogenous CD28 antigen from binding its endogenous ligand. This step comprises contacting a B7-positive cell with a soluble ligand which recognizes and binds the B7 antigen. Examples include CTLA4Ig, soluble CD28 molecules, and antibodies directed against B7 such as BB-1.

The binding of the gp39-positive cell to its soluble ligand blocks the reaction of gp39 antigen with endogenous CD40. The binding of the B7-positive cell to its soluble ligand blocks the reaction of the B7 antigen with endogenous CD28. This combined blockage inhibits the immune response.

In another example, endogenous CD40 antigen is prevented from binding its endogenous ligand as described above. The example provides the additional step of preventing the endogenous B7 antigen from binding its endogenous ligand. This comprises contacting a CD28-positive cell with a soluble ligand which recognizes and binds the CD28 antigen. Examples of such soluble ligands include soluble B7 molecules and antibodies directed against CD28.

The binding of the CD40-positive cell to the soluble ligand blocks the reaction of CD40 antigen with endogenous gp39. The binding of the CD28-positive cell to the soluble ligand blocks the reaction of the B7 antigen with endogenous CD28. This combined blockage inhibits the immune response.

In yet another example, endogenous CD40 antigen is prevented from binding its ligand as described above. This example provides the additional step of preventing the endogenous B7 antigen from binding its endogenous ligand which comprises contacting a CTLA4-positive cell with a soluble ligand which recognizes and binds the CTLA4 antigen. Examples of such soluble ligands include soluble B7 molecules and antibodies directed against CTLA4.

The binding of the CD40-positive cell to the soluble ligand blocks the reaction of CD40 antigen with endogenous gp39. Additionally, the binding of the CTLA4- or CD28-positive cell to the soluble ligand blocks the reaction of the CTLA4 antigen with endogenous B7. This combined blockage inhibits the immune response.

In a further example, endogenous CD40 antigen is prevented from binding its ligand as described above. This example provides the additional step of preventing the endogenous B7 antigen from binding its endogenous ligand which comprises contacting a CD28-positive cell with a soluble ligand which recognizes and binds the CD28 antigen. Examples of such soluble ligands include soluble B7 molecules and antibodies directed against CD28.

The binding of the CD40-positive cell to the soluble ligand blocks the reaction of gp39 antigen with endogenous CD40. Further, the binding of the CD28-positive cell to the soluble ligand blocks the reaction of the CD28 antigen with endogenous B7. This combined blockage inhibits the immune response.

Also, in another example, endogenous CD40 antigen is prevented from binding its ligand as described above. This example provides the additional step of preventing the endogenous B7 antigen from binding its endogenous ligand which comprises contacting a CTLA4-positive cell with a soluble ligand which recognizes and binds the CTLA4 antigen.

The binding of the CD40-positive cell to the soluble ligand blocks the reaction of gp39 antigen with endogenous CD40. Additionally, the binding of the CTLA4-positive cell to the soluble ligand blocks the reaction of the CTLA4 antigen with endogenous B7. This combined blockage inhibits the immune response.

Additionally, the present invention provides another embodiment for a method for inhibiting an immune response resulting in graft rejection. This embodiment comprises contacting a B7-positive cell with a first soluble ligand which recognizes and binds the B7 antigen, and contacting a gp39-positive cell with a second soluble ligand which recognizes and binds the gp39 antigen.

The binding of the B7-positive cell to the first soluble ligand blocks the reaction of the B7 antigen with endogenous CTLA4 or CD28. Further, the binding of the gp39 antigen to the second soluble ligand blocks the reaction of gp39 antigen with endogenous CD40. The combination of this blockage inhibits the immune response.

Additionally, the invention provides a method for inhibiting an immune response mediated by the CTLA4/CD28/B7 and gp39/CD40 pathways in a subject. In accordance with the practice of the invention, the subject may be an animal subject such as a human, a dog, a cat, a sheep, a horse, a mouse, a pig, or a cow.

The method comprises administering to the subject a first soluble ligand which recognizes and binds the B7 antigen (e.g. soluble CTLA4 or CD28 molecules) and a second soluble ligand which recognizes and binds the gp39 antigen (e.g., monoclonal antibodies directed against gp39 (MR1) or soluble CD40 molecules). The binding of the first and second ligands to their receptor inhibits the immune response mediated by CTLA4-, CD28-, and gp39- cell interactions with B7- and CD40-positive cells.

Also, the invention provides a method for inhibiting transplant rejection in a subject. This method comprises administering to the subject an effective amount of a combination of a first soluble ligand which recognizes and binds the B7 antigen on B7-positive cells and a second soluble ligand which recognizes and binds the gp39 antigen on gp39-positive cells. The binding of B7-positive cells with the first soluble ligand and gp39-positive cells with the second soluble ligand disrupts endogenous CTLA4-, CD28-, and gp39- cell interactions with B7-positive cells and gp39-positive cells so that transplant rejection is inhibited.

In accordance with the practice of the invention, the first soluble ligand may be a recombinant binding molecule having at least a portion of the extracellular domain of CTLA4. In accordance with the practice of the invention, the extracellular portion of CTLA4 is joined to a non-CTLA4 protein sequence. The non-CTLA4 protein sequence may be at least a portion of an immunoglobulin molecule.

In one specific example of the invention, the ligand is CTLA4Ig fusion protein, e.g., the CTLA4Ig fusion protein deposited with the American Type Culture Collection (ATCC) in Rockville, Md., under the provisions of the Budapest Treaty on May 31, 1991 and accorded ATCC accession number: 68629. Alternatively, the ligand may be a CD28Ig/CTLA4Ig fusion protein hybrid (U.S. Pat. No. 5,434,131, issued Jul. 18, 1995).

In an alternative embodiment, the first soluble ligand may be a monoclonal antibody reactive with B7 antigen, e.g., the antibody may be anti-BB1 monoclonal antibody (Clark et al., Human Immunol. 16:100–113 (1986); Yokochi et al., J. Immunol. 128:823 (1981)); Freeman et al. (J. Immunol. 143(8):2714–2722 (1989); and Freedman et al., J. Immunol. 139:3260 (1987)).

In another embodiment, the ligand may be a CD28Ig/CTLA4Ig fusion protein hybrid having a first amino acid sequence corresponding to a portion of the extracellular domain of CD28 receptor fused to a second amino acid sequence corresponding to a portion of the extracellular domain of CTLA4 receptor and a third amino acid sequence corresponding to the hinge, CH2 and CH3 regions of human immunoglobulin Cγ1.

In one embodiment of the invention, the second soluble ligand for the gp39 antigen may be a monoclonal antibody reactive with the gp39 antigen, e.g., the MR1 anti-murine monoclonal antibody or the anti-human gp39 antibody (U.S. Pat. No. 5,474,771, issued Dec. 12, 1995).

In another embodiment of the invention, the method comprises administering to the subject a soluble fusion protein, the soluble fusion protein comprising a first binding domain and a second binding domain.

In one example, the first binding domain is a ligand which recognizes and binds the gp39 antigen. Examples include CD40 and monoclonal antibodies directed against gp39. In another example, the first binding domain is a ligand which recognizes and binds the CD40 antigen. Examples include gp39 and monoclonal antibodies directed against CD40.

In one example, the second binding domain is a ligand which recognizes and binds CTLA4. Examples include B7 and monoclonal antibodies directed against CTLA4. In another example, the second binding domain is a ligand which recognizes and binds the CD28 antigen. Examples include B7 and monoclonal antibodies directed against CD28. In another example, the second binding domain is a ligand which recognizes and binds the B7 antigen. Examples include CTLA4, CD28 and monoclonal antibodies directed against B7.

Soluble ligands may be administered during transplant, before transplant, or after transplant. Soluble ligands may be administered by oral means, transdermal means, intravenous means, intramuscular means, intraperitoneal, or by subcutaneous administration.

The most effective mode of administration and dosage regimen for the molecules of the present invention depends upon the location of the tissue or disease being treated, the severity and course of the medical disorder, the subject's health and response to treatment and the judgment of the treating physician. Accordingly, the dosages of the molecules should be titrated to the individual subject.

By way of example, the interrelationship of dosages for animals of various sizes and species and humans based on $mg/m^2$ of surface area is described by Freireich, E. J., et al. Cancer Chemother., Rep. 50 (4):219–244 (1966). Adjustments in the dosage regimen may be made to optimize suppression of the immune response resulting in graft rejection, e.g., doses may be divided and administered on a daily basis or the dose reduced proportionally depending upon the situation (e.g., several divided doses may be administered daily or proportionally reduced depending on the specific therapeutic situation).

It would be clear that the dose of the composition of the invention required to achieve an appropriate clinical outcome may be further reduced with schedule optimization.

The present invention also provides pharmaceutical compositions useful in inhibiting graft rejection or in inhibiting an immune response. In one embodiment, these compositions comprise an effective amount of a combination of (a) soluble ligands which recognize and bind any one of CTLA4, CD28, and B7 antigens, together with (b) soluble ligands which recognize and bind any one of gp39 and CD40 antigens and an acceptable carrier. In another embodiment, these compositions comprise an effective amount of a soluble fusion protein comprising a first binding domain and a second binding domain, wherein the first binding domain is a ligand which recognizes and binds any one of gp39 or CD40 antigens and the second binding domain is a ligand which recognizes and binds any one of CTLA4, CD28, and B7 antigens.

ADVANTAGES OF THE INVENTION: Despite the many advances in clinical immunosuppression, chronic vascular rejection remains the major source of transplant failure for which there remains no effective therapy. The experiments described herein show that blocking the CD28/CTLA4/B7 and gp39/CD40 pathways inhibits the development of chronic transplant vasculopathy in transplanted tissues. These data show that immune responses to allogeneic and xenogeneic grafts can be inhibited without cytoablation. When compared to the use of soluble CTLA4 molecules alone, the use of soluble CTLA4 molecules together with a soluble ligand that recognizes and binds gp39 provides dramatically prolonged immunosuppression.

The following examples are presented to illustrate the present invention and to assist one of ordinary skill in making and using the same. The examples are not intended in any way to otherwise limit the scope of the invention.

EXAMPLE 1

The data in this example show that simultaneous blockade of CD28 and CD40 signals ablates popliteal lymph node alloimmune responses in vivo.

Method

Male C3H/HeJ (The Jackson Laboratory, Bar Harbor, ME) mice were subcutaneously immunized with $2\times10^6$ BALB/c splenocytes in 50 μl of sterile normal saline in the left foot pad and 50 μl of sterile normal saline in the right foot pad on day 0 and then treated intraperitoneally with MR1 (250 μg), CTLA4Ig (250 μg), or both reagents on days 0, 2 and 4.

The mice were sacrificed on day 5, the popliteal lymph nodes were harvested using an operating microscope (20X magnification) and the fresh weight of each node was determined to the nearest 0.1 mg with an analytical balance (Model A-160, Denver Instrument Company, Arvada, Colo.).

Discussion

Five days after subcutaneous immunization with allogeneic splenocytes, the draining popliteal lymph nodes on the side of antigen challenge underwent a >5 fold increase in weight relative to the contralateral node in untreated control mice. Treatment with either CTLA4Ig or MR1 resulted in a 50–60% inhibition of the response, whereas concomitant administration of CTLA4Ig and MR1 ablated lymph node expansion in response to antigen challenge. The results represent the mean±standard deviation for 3 individual mice in each group. Similar results were obtained in three independent experiments.

Control mice demonstrated a 4–6 fold increase in the weight of the node draining the immunized foot relative to the node draining the contralateral foot injected with sterile saline (FIG. 1). This increase in weight was accompanied by a dramatic expansion of the lymphocyte-rich paracortical (T cell) and cortical (B cell) regions. When administered alone, CTLA4Ig and MR1 each produced partial inhibition of this response (57% and 56% inhibition, respectively). The combination of CTLA4Ig/MR1 ablated lymph node expansion (98% inhibition, FIG. 1) and prevented expansion of the paracortical and lymphoid follicles.

EXAMPLE 2

This example shows prolongation of cardiac allograft survival and inhibition of vasculopathy associated with chronic rejection.

Method

Male C3H/HeJ mice were transplanted with primarily vascularized BALB/c heart allografts at 8–12 weeks of age using microsurgical techniques (Corry, R. J., Winn, H. J. & Russell, P. S. Transplantation 16, 343–350 (1973)).

Rejection was defined by the loss of palpable cardiac contractions with confirmation at laparotomy by direct visualization. At specified times after transplant, the transplanted hearts were excised, formalin fixed and embedded in paraffin. Tissue sections (5 $\mu$m) were stained with Masson's Trichrome or hematoxylin-eosin. Each histologic specimen was reviewed by a cardiac transplant pathologist (KJW) blinded to the treatment modality.

Discussion

Figure 2A:
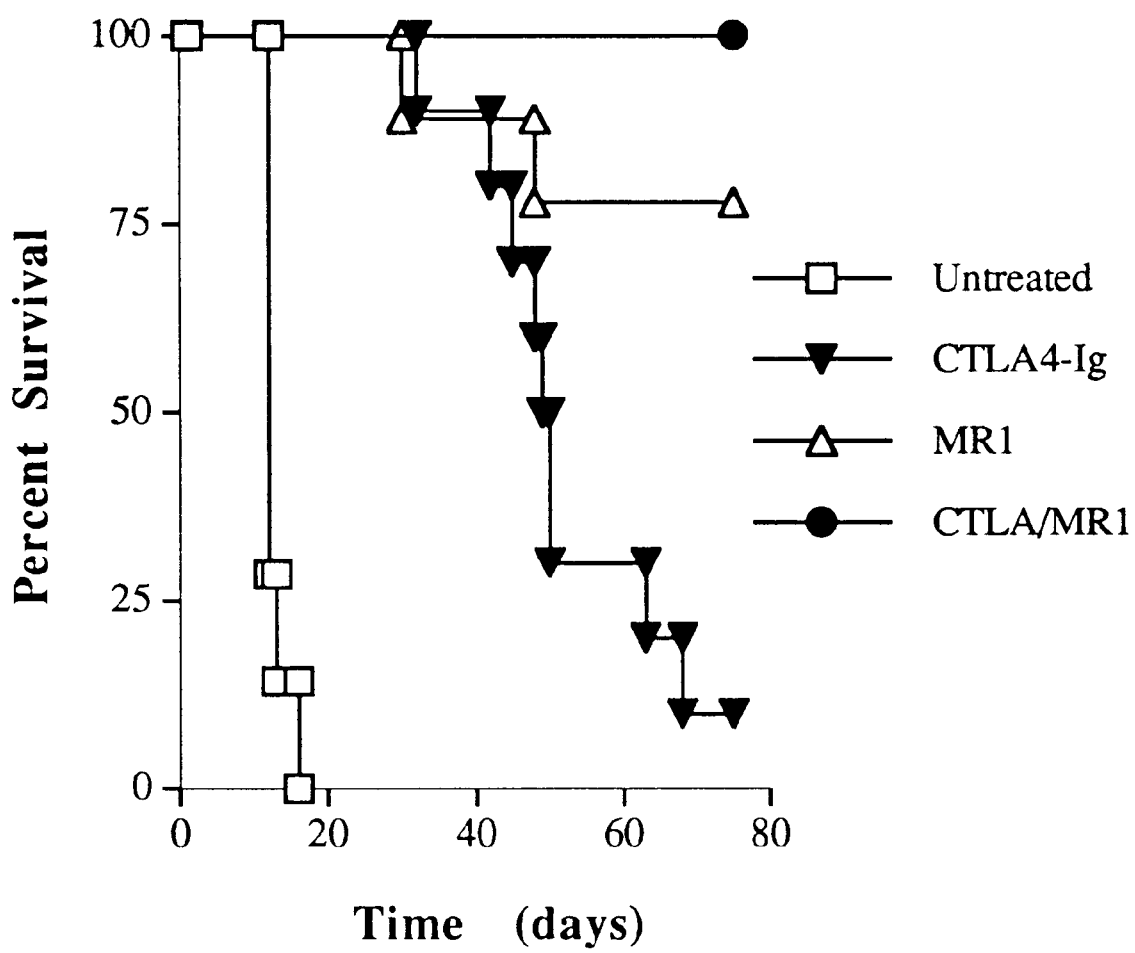
FIG. 2A is a line graph that shows CTLA4Ig/MR1 treatment prolongs cardiac allograft survival in comparison with CTLA4Ig or MR1 alone.

In FIG. 2A C3H/HeJ recipients were treated with CTLA4Ig (200 $\mu$g/dose) on days 0, 2, 4 and 6 combined with MR1 (250 $\mu$g/dose) on days 0, 2 and 4, and had long term survival of BALB/c cardiac allografts (Median Survival Time (MST)>70 days, n=7). The control groups included recipients treated with: CTLA4Ig alone (MST=50 days, n=12); MR1 alone (MST=70 days, n=12); and no treatment (MST=12 days, n=7).

All recipients were followed for 70 days with the exception of three mice with surviving transplants in each experimental group which were sacrificed for histologic analysis at 58–63 days post transplant.

Figure 2B:
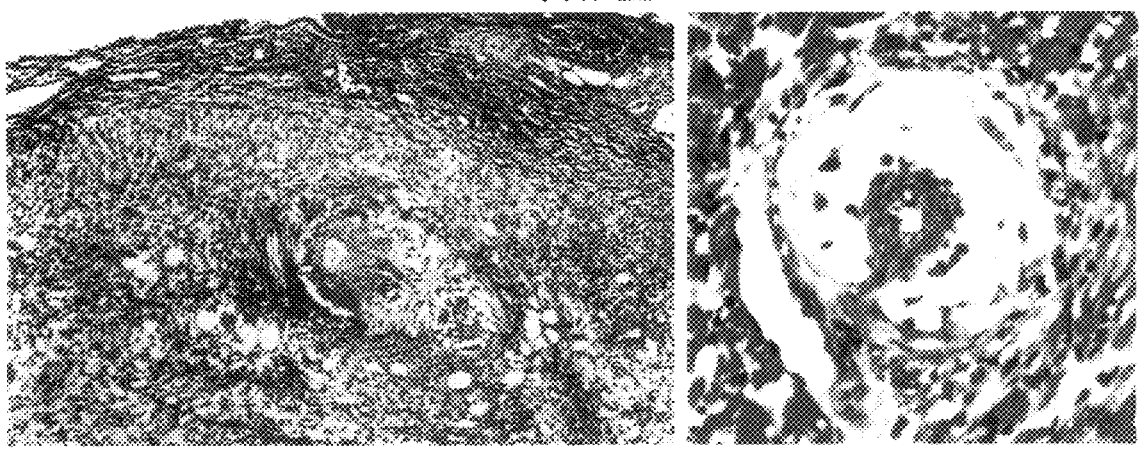
FIG. 2B is a photograph of a histologic section showing CTLA4Ig-treated cardiac allograft at day 62 having extensive lymphocytic infiltration, interstitial fibrosis, and severe coronary arterial intimal thickening and fibrosis consistent with chronic rejection (left panel 100X magnification; right panel 400X magnification).

In FIG. 2B, CTLA4Ig-treated cardiac allograft at day 62 shows extensive lymphocytic infiltration, interstitial fibrosis, and severe coronary arterial intimal thickening and fibrosis consistent with chronic rejection.

Figure 2C:
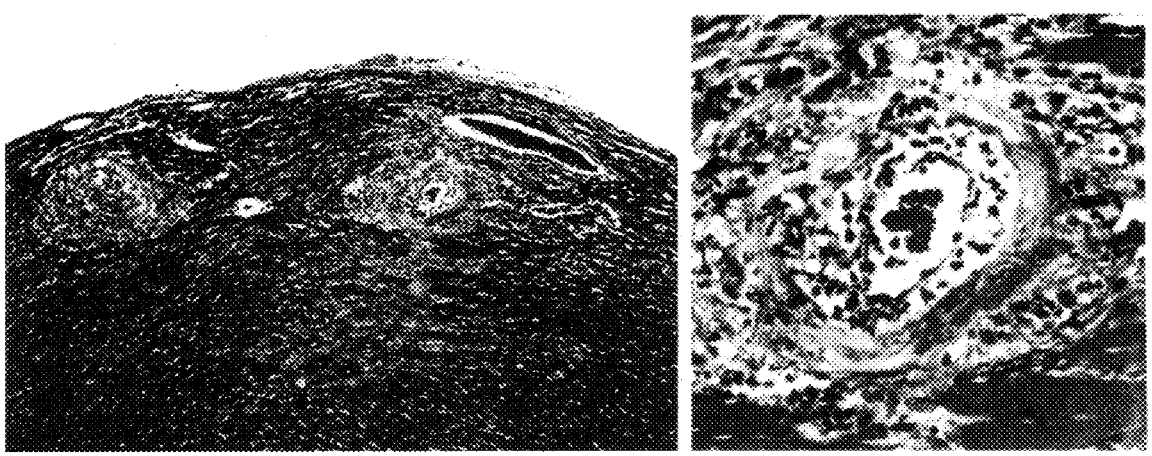
FIG. 2C is a photograph of a histologic section showing a MR1-treated cardiac allograft at day 62 having less lymphocytic infiltration and interstitial fibrosis, but severe coronary vasculopathy characteristic of chronic rejection (left panel 100X magnification; right panel 400X magnification).

In FIG. 2C, MR1-treated cardiac allograft at day 62 demonstrates less lymphocytic infiltration and interstitial fibrosis, but severe coronary vasculopathy characteristic of chronic rejection.

Figure 2D:
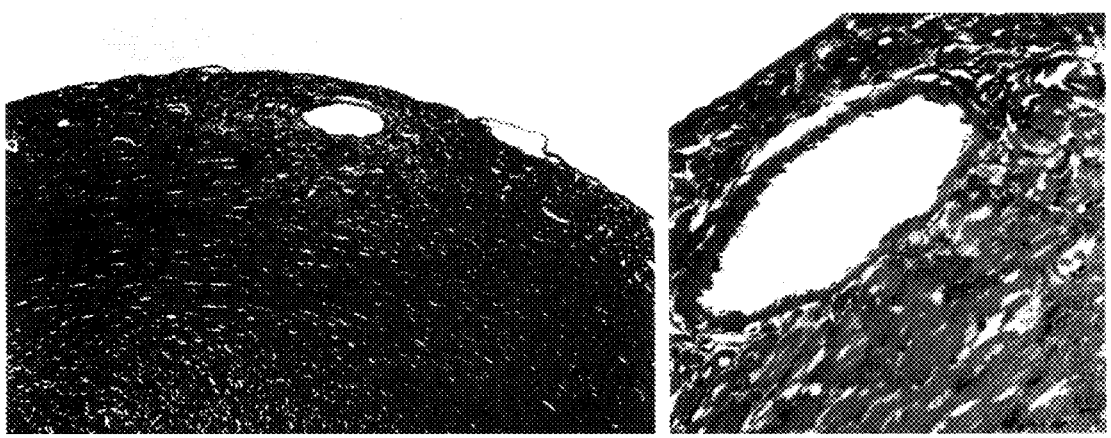
FIG. 2D is a photograph of a histologic section showing CTLA4Ig/MR1-treated cardiac allografts at day 58, free from lymphocytic infiltration, fibrosis, coronary arterial intimal lesions (left panel 100X magnification; right panel 400X magnification).

In FIG. 2D, CTLA4Ig/MR1-treated cardiac allografts at day 58, in marked contrast, were remarkably free from lymphocytic infiltration, fibrosis, and most significantly, coronary arterial intimal lesions. The parenchyma and blood vessels of these grafts were virtually indistinguishable from normal untransplanted BALB/c hearts.

Figure 2E:
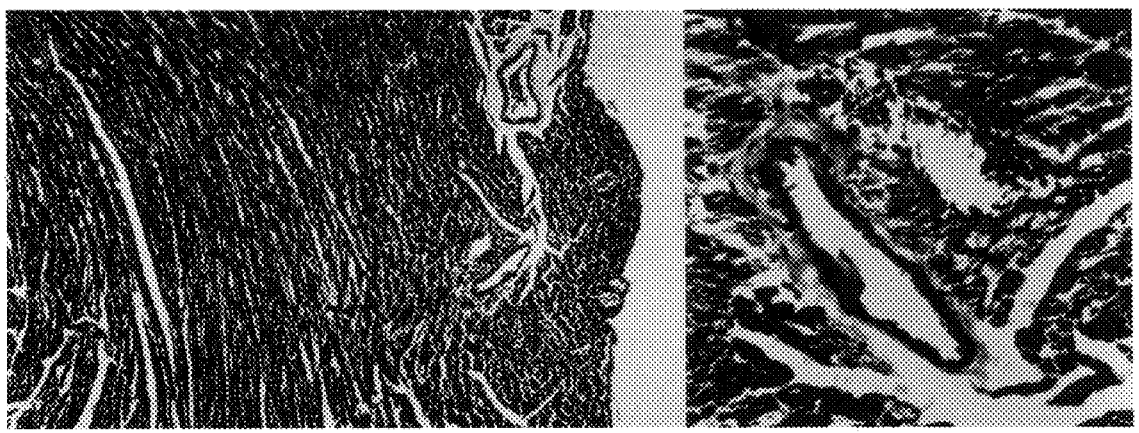
FIG. 2E is a photograph of a histologic section showing normal untransplanted BALB/c hearts (left panel 100X magnification; right panel 400X magnification).

In FIG. 2E, normal untransplanted BALB/c hearts are shown.

Similar histologic results were obtained from three allografts in each experimental group. C3H/HeJ (H-2$^k$) recipients treated with CTLA4Ig alone, MR1 alone, or CTLA4Ig/MR1, all showed prolonged survival of BALB/c (H-2$^d$) cardiac allografts when compared to untreated controls (FIG. 2A). However, when examined histologically at 58–62 days post-transplant marked differences were apparent.

Allografts from CTLA4Ig-treated recipients showed extensive lymphocytic infiltration, interstitial fibrosis, and severe coronary arterial intimal thickening and fibrosis consistent with chronic rejection (FIG. 2B). While the MR1-treated allograft demonstrated less lymphocytic infiltration and interstitial fibrosis, these grafts also had severe coronary vasculopathy characteristic of chronic rejection (FIG. 2C).

In marked contrast, the allograft from CTLA4Ig/MR1 treated recipients were remarkably free from lymphocytic infiltration, fibrosis, and most significantly, coronary arterial intimal lesions (FIG. 2D). In fact, the parenchyma and blood vessels of these grafts were virtually indistinguishable from those found in normal BALB/c hearts (FIG. 2E).

EXAMPLE 3

This example shows blockade of T cell cytokine and costimulatory molecule transcript expression.

Method

At 8 days after transplantation, the cardiac grafts were removed and total RNA was prepared from tissues using TRIzol Reagent (GIBCO BRL, Gaithersburg, Md.). cDNA was synthesized using 5 $\mu$g of total RNA template with a Superscript Preamplification System (GIBCO BRL, Gaithersburg, Md.) in a final volume of 20 $\mu$l. PCR reactions were carried out. PCR products were visualized on ethidium bromide stained 1% agarose (BIO-RAD, Hercules, Calif.), 2% NuSieve GTG agarose (FMC BioProducts, Rockland, Me.) gels. Gel images were stored using a UVP Gel Documentation System 5000. Band intensity was quantified using Gelreader analysis software (National Center for Supercomputing Applications, Urbana, Ill.).

Figure 3A:
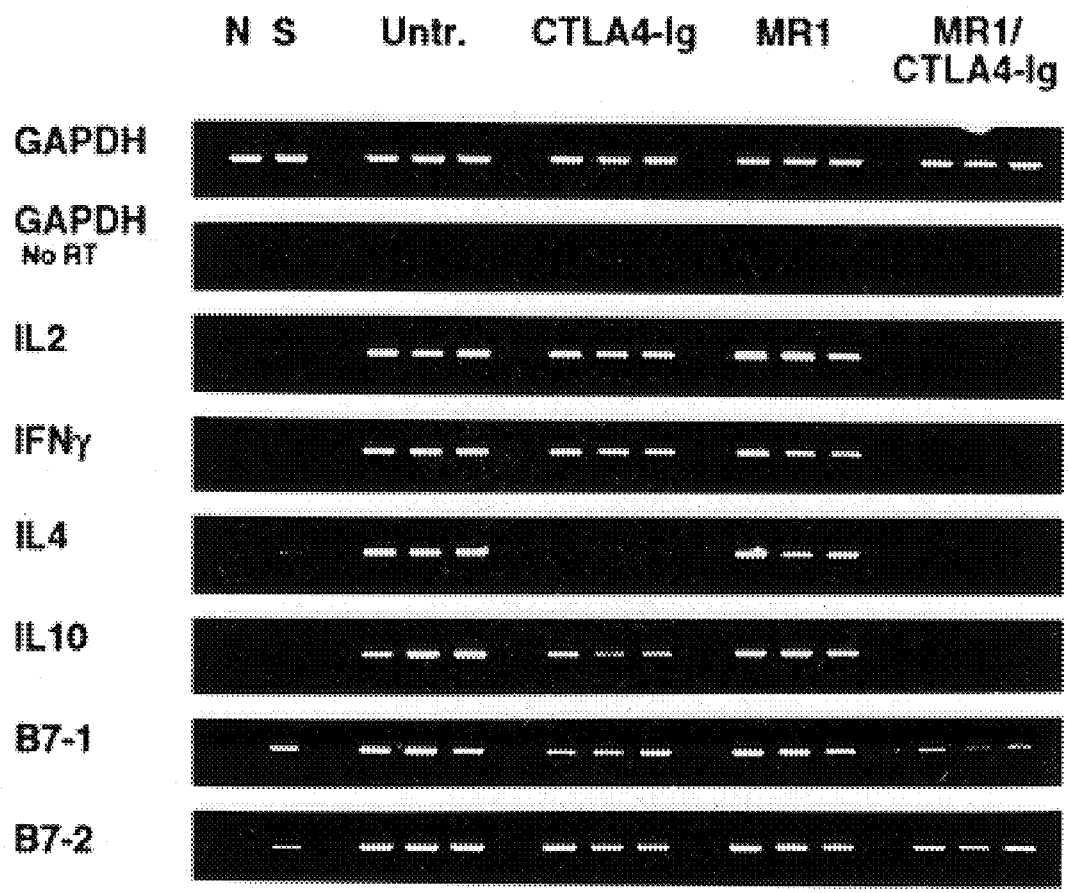
FIG. 3A is a photograph of ethidium bromide stained gel strips showing intragraft expression of immune mediator transcripts using RT-PCR in untreated, MR1 treated, CTLA4Ig treated, and MR1/CTLA4Ig treated cardiac allografts.

In FIG. 3A, intragraft expression of immune mediator transcripts was assessed using RT-PCR in untreated, MR1-treated, CTLA4Ig treated, and MR1/CTLA4Ig treated cardiac allografts.

Three allografts from each treatment group and the control group were analyzed at 8 days post-transplant. Normal heart tissue (N) and a syngeneic heart graft (S) at 8 days after transplantation were included for comparison.

Figure 3B:
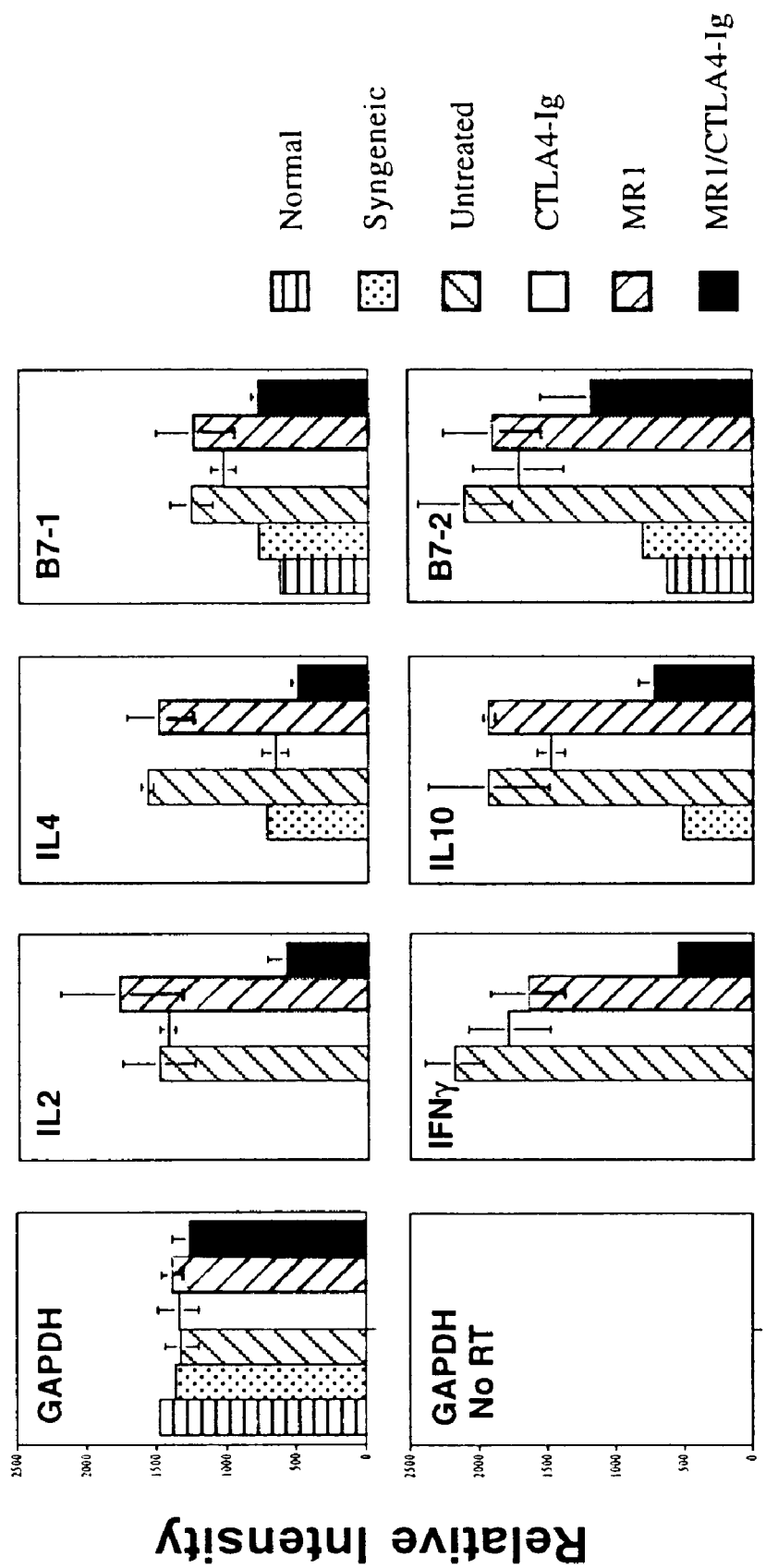
FIG. 3B is a series of bar graphs showing the mean PCR product band intensities±standard deviation.

In FIG. 3B, graphical representation of the mean PCR product band intensities±standard deviation are shown.

Discussion

No consistent differences in the expression of T cell cytokine transcripts for IL-2, IL-4, IL-10, and IFN$\gamma$ or costimulatory molecule transcripts (B7-1, and B7-2) were detectable between the control allografts (FIG. 3A, untreated) and MR1-treated allografts (FIG. 3A), whereas CTLA4Ig partially inhibited expression of IL-4 transcripts.

Allografts from CTLA4Ig/MR1-treated recipients showed a striking decrease in the expression of both Th1 cytokine (IL-2 and IFN$\gamma$) and Th2 cytokine (IL-4, and IL-10) transcripts. However, intragraft B7-1 and B7-2 costimulatory molecule transcripts were only modestly reduced in recipients treated with CTLA4Ig/MR1.

PCR reactions using template prepared without reverse transcriptase yielded no products, even for the intron-less GADPH gene (FIG. 3A, GADPH, NO RT), confirming the absence of contaminating genomic DNA.

Intragraft B7-1 and B7-2 costimulatory molecule transcripts were only modestly reduced in recipients treated with CTLA4Ig/MR1, (FIG. 3) suggesting that CD28/B7-independent or CD40/gp39-independent factors, such as GMCSF (Larsen, C. P., et al. J Immunol 152, 5208–5219 (1994)), may be important regulators of intragraft B7 expression. Thus, MR1-mediated blockade of the CD40 pathway not only inhibits T cell cognate help for effector APC's, but enhances the ability of CTLA4Ig to inhibit T cell activation transcript expression within allografts. These data are consistent with those from our studies in vitro which indicate that while MR1 alone has only a modest negative effect on cellular proliferation in allogeneic mixed leukocyte reactions, it potentiates the inhibitory effects of suboptimal concentrations of CTLA4Ig.

EXAMPLE 4

This example demonstrates prolongation of murine skin allograft survival using C3H/HeJ mice which received full thickness skin allografts from BALB/c mice.

Method

Segments of either full thickness tail or ear skin of approximately 1 cm square were grafted on to the posterior-lateral thoracic wall of recipient mice and secured in place with a circumferential Bandaid®. The grafts were then followed by daily visual inspection. Rejection was defined as the complete loss of visible epidermal graft tissue. Treatment protocols for MR1 and CTLA4Ig were as detailed for heart transplant recipients in FIG. 1. CyA (Sandoz, East Hanover, N.J.) at a concentration of 50 mg/ml was administered at a rate of 0.5 $\mu$l/hr (~20 mg/kg/day) for 14 days via an osmotic pump (Alzet Model No. 2002, Alza, Palto Alto, Calif.) which was implanted subcutaneously in the dorsal region of the recipient at the time of skin grafting and removed at 21 days after transplant (Pereira, G. M., Miller, J. F. & Shevach, E. M. J Immunol 144, 2109–2116 (1990)). After sacrifice, the skin graft was excised, formalin fixed and embedded in paraffin. Tissue sections (5 $\mu$m) were stained with hematoxylin-eosin.

Figure 4A:
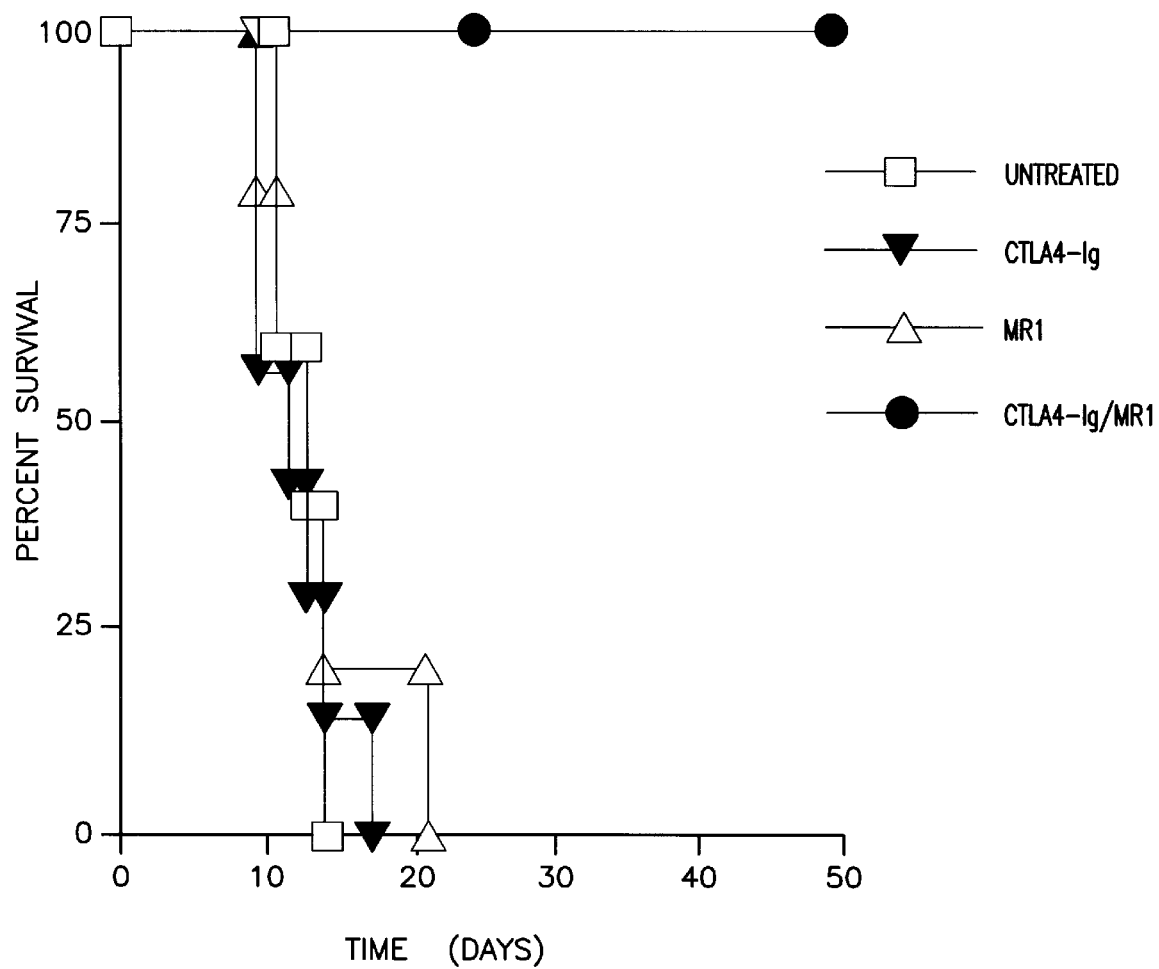
FIG. 4A is a line graph showing data of mice treated with MR1 alone, CTLA4Ig alone, and a combination of MR1 and CTLA4Ig.

In FIG. 4A, C3H/HeJ recipients treated with either MR1 alone (MST 13 days, n=5) or CTLA4Ig alone (MST=12 days, n=7) rejected fully MHC-disparate BALB/c skin grafts at the same rate as an untreated control group (MST=13 days, n=5). In contrast, when MR1 and CTLA4Ig were administered together in the perioperative period, the allografts enjoyed markedly prolonged survival (MST>50, n=15).

Figure 4B:
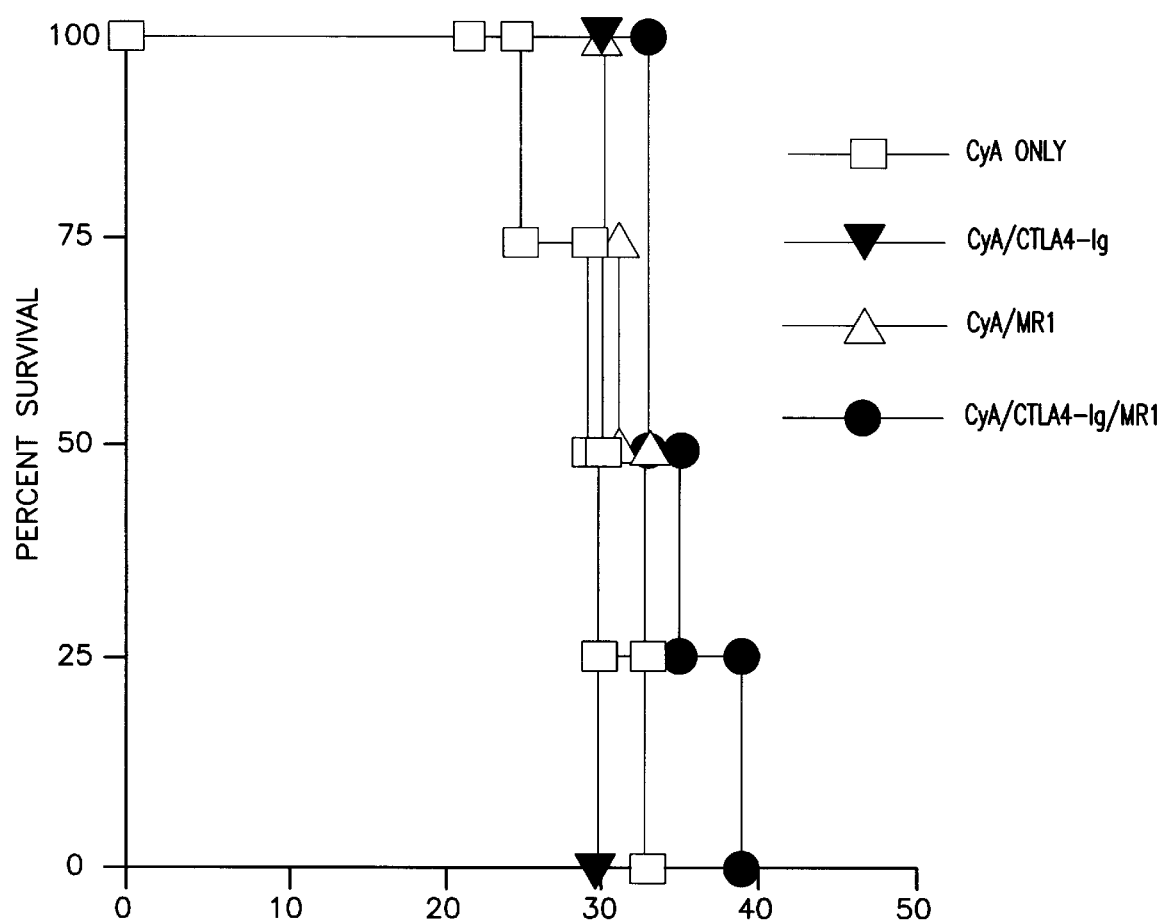
FIG. 4B is a line graph showing data of mice treated with CyA, CyA and CTLA4Ig, and CyA and MR1.

In FIG. 4B, mice treated with CyA alone (MST=30 days, n=4), CyA plus CTLA4Ig (MST=30 days, n=5), or CyA and MR1 (MST=32 days, n=4) all displayed similar modestly prolonged skin graft survival. Surprisingly, the salutary effect of CTLA4Ig/MR1 on skin graft survival was abolished by concomitant cyclosporine administration (MST=34 days, n=4).

Figure 4C:
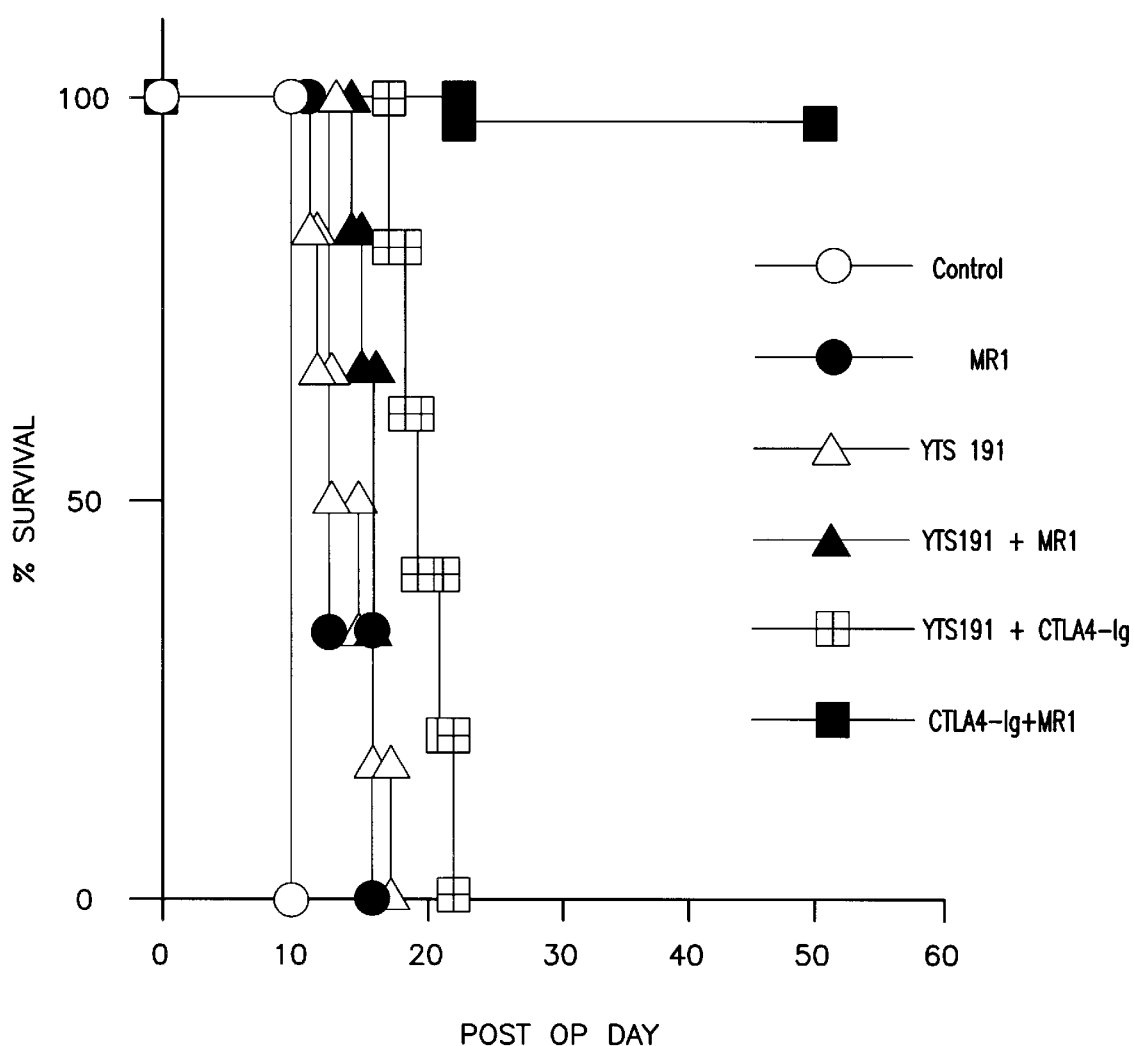
FIG. 4C is a line graph showing the effects of perioperative treatment with YTS191 and MR1, alone, MR1 and CTLA4Ig, and YTS191 and CTLA4Ig on primary skin allografts.

In FIG. 4C, C3H recipients of BALB/c skin grafts were not treated (MST 10d, n=3), or treated with MR1 (MST 13d, n=3), YTS191.1 (MST 14d, n=6), YTS191.1 and MR1 (MST 16d, n=6), YTS191.1 and CTLA4Ig (MST 19d, n=5), or CTLA4Ig and MR1 (MST>50d, n=22). Thus far, >53 mice have been treated with CTLA4Ig/MR1. Of these, 2 died on days 13 and 21. All others have remained healthy throughout the experiments without signs of weight loss, infection, or malignancy.

Figures 4D, 4E:
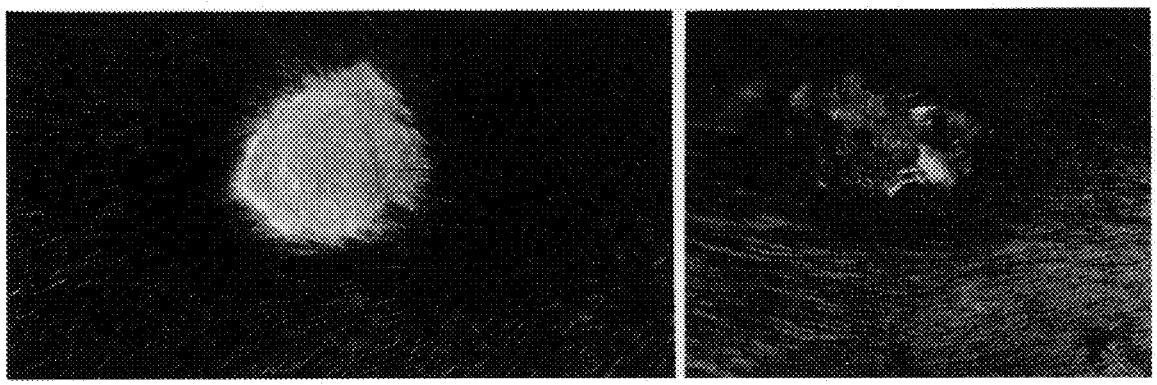
FIG. 4D is a photograph showing healthy appearance of a BALB/c skin graft on a CTLA4Ig/MR1 treated recipient.
FIG. 4E is a photograph showing a control allograft undergoing rejection.
Figure 4F:
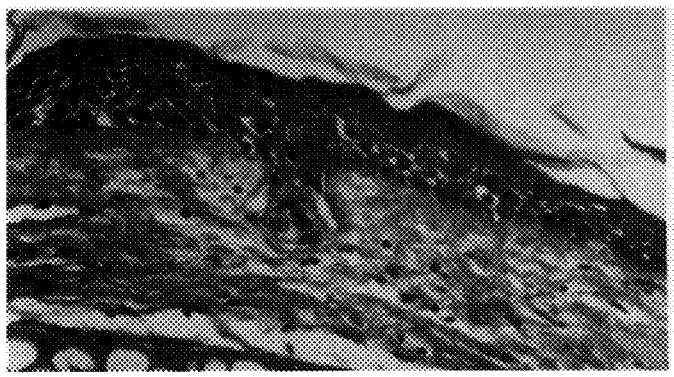
FIG. 4F is a photograph of a histologic section of a skin graft showing healthy appearance of an accepted graft at 100 days after transplant showing well preserved epidermis hair follicles and adnexal structures.
Figure 4G:
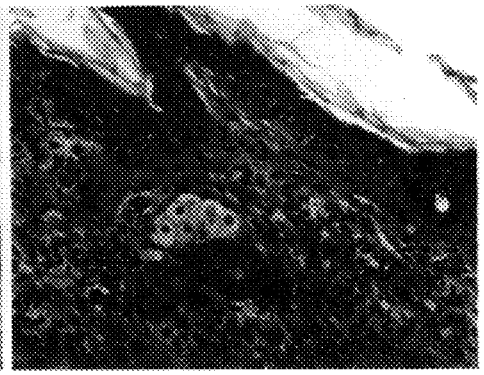
FIG. 4G is a photograph showing a BALB/c skin graft on an untreated recipient eight days after transplant. The graft shows extensive lymphocytic infiltrate.

Healthy appearance of a BALB/c skin graft on an CTLA4Ig/MR1 treated C3H/HeJ recipient at 50 days after transplant (FIG. 4D), contrasts sharply with a control allograft undergoing rejection (FIG. 4E). On hematoxylin-eosin stained sections the accepted graft at 100 days after transplant demonstrated well preserved epidermis, hair follicles and adnexal structures (FIG. 4F), which is in contrast to a BALB/c skin graft on an untreated C3H/HeJ recipient 8 days after transplant which shows an extensive lymphocytic infiltrate (FIG. 4G).

Discussion

The effects of CTLA4Ig and MR1, alone and in combination on primary skin allograft survival in mice were tested (FIG. 4). For comparison, recipients were also treated with CyA alone or CyA combined with either CTLA4Ig or MR1. C3H/HeJ recipients treated with either MR1 alone or CTLA4Ig alone rejected fully MHC-disparate BALB/c skin grafts at the same rate as untreated controls (FIG. 4A).

Mice treated with CyA alone, CyA plus CTLA4Ig, or CyA and MR1 all displayed modestly prolonged skin graft survival (FIG. 4B). However, all of these allografts were ultimately rejected with no apparent effects between either drug and CyA.

As a rigorous test of the ability of CD40/CD28 blockade to interrupt alloimmune responses, we studied the effects of perioperative treatment with CTLA4Ig and MR1, alone and in combination on primary skin allograft survival in mice. For comparison, recipients were also treated with CyA, an anti-CD4 mAb YTS191.1, or with either of these agents combined with CTLA4Ig or MR1 (FIGS. 4B and 4C). C3H/HeJ recipients treated with either MR1, CTLA4Ig, or YTS191.1 alone rejected fully MHC-disparate BALB/c skin grafts at essentially the same rate as untreated controls (FIGS. 4B and 4C). Mice treated with YTS191.1 and MR1, YTS191.1 and CTLA4Ig, CyA alone, CyA plus CTLA4Ig, or CyA and MR1 displayed modestly prolonged skin graft survival (FIGS. 4B and 4C). However, all of these allografts were ultimately rejected.

In contrast, on recipients treated with both MR1 and CTLA4Ig in the perioperative period, the skin allografts demonstrated markedly prolonged survival. Visual examination of these allografts at 50 days after transplantation showed the grafts to be healthy in appearance, well vascularized, supple, and bearing short white hair (FIG. 4D). Histologically, the accepted grafts demonstrated well preserved epidermis, hair follicles and adnexal structures (FIG. 4F). Surprisingly, the salutary effect of CTLA4Ig/MR1 on skin graft survival was abolished by concomitant cyclosporine administration (FIG. 4B).

The remarkable potency of this effect was most clearly evident in the primary skin allograft model. Neither CTLA4Ig or MR1 alone or with CyA significantly prolonged skin allograft survival. Only the combination of CTLA4Ig and MR1 produced >50 day survival of fully-MHC mismatched skin allografts. Similar prolongation in this stringent test of inhibition of the alloimmune response has previously only been observed using vigorous cytoablative and/or hematopoietic chimerism-based strategies (Mayumi, H. & Good, R. A. J Exp Med 169, 213–238 (1990); Ildstad, S. T. & Sachs, D. H., Nature 307, 168–170 (1984); Ilstad, S. T., et al. J Exp Med 162, 231–44 (1985); Cobbold, S. P., Martin, G., et al. Nature 323, 164–166 (1986); Qin, S., et al. Science 259, 974–977 (1993)).

EXAMPLE 5

To explore the effect of blockade of the CD28 and CD40 pathways on T cell proliferation, we studied the primary allogeneic mixed leukocyte reaction using T cells from both Ie$^k$-restricted pigeon cytochrome c-reactive (pcc-TCRTg) and L$^d$-alloreactive (2C) T cell receptor transgenic mice (REF HED and LOH). CTLA4Ig, a fusion protein which binds to the ligands for CD28 and its homologue CTLA4, effectively inhibited proliferation of all three T cell populations (FIG. 5A).

Figure 5A:
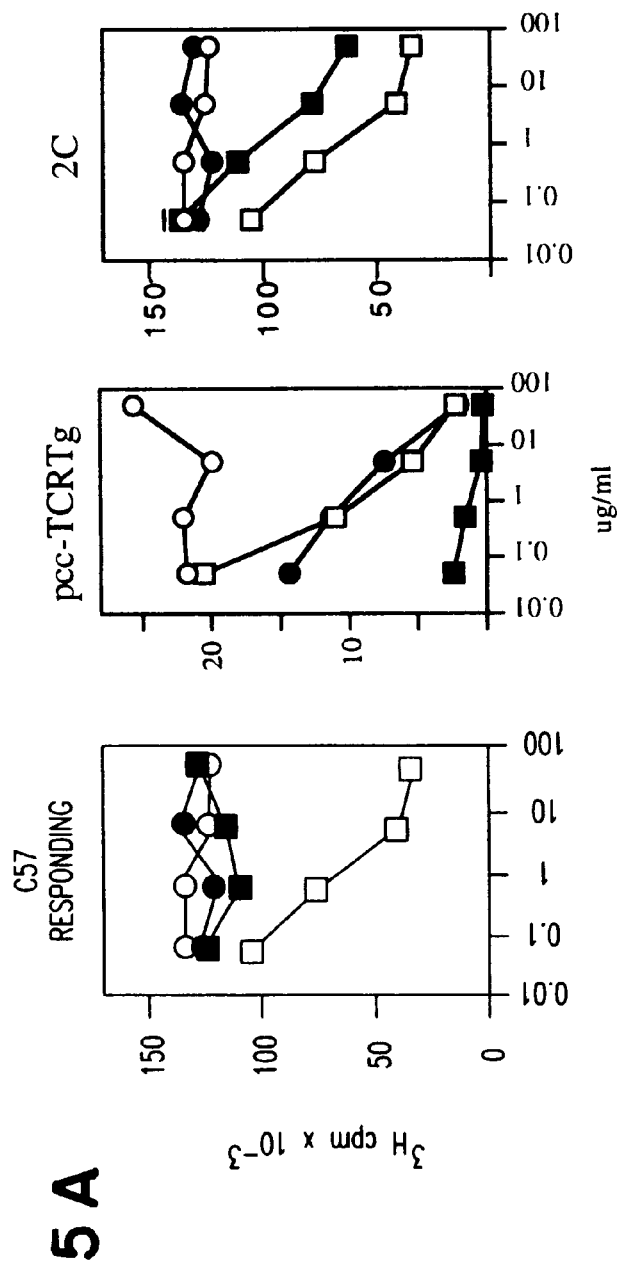
FIG. 5A is a series of line graphs showing the effects in vitro of using MR1 alone, CTLA4Ig alone, and a combination of MR1/CTLA4Ig on three different cell populations.

In contrast, blockade of the CD40 pathway with the hamster anti-gp39 mAb, MR1, modestly (~50%) inhibited the proliferation of C3H/HeJ T cells responding to BALB/c dendritic cells, dramatically inhibited ($\geq$85%) pcc-TCRTg T cells to reacting to cytochrome c, but had negligible effects on the proliferation of 2C T cells responding to L$^d$-bearing BALB/c dendritic cells (FIG. 5A).

Furthermore, simultaneous blockade with these agents cooperatively inhibited T cell proliferation in allogeneic mixed leukocyte reactions and pcc-TCRTg T cells, whereas MR-1 had no effect or slightly augmented the proliferation of 2C T cells when combined with CTLA4Ig (FIG. 5A). These results indicate that not all T cells are dependent on CD40 signals for clonal expansion and may explain the inability of CD40 blockade to completely inhibit allograft rejection.

Figure 5B:
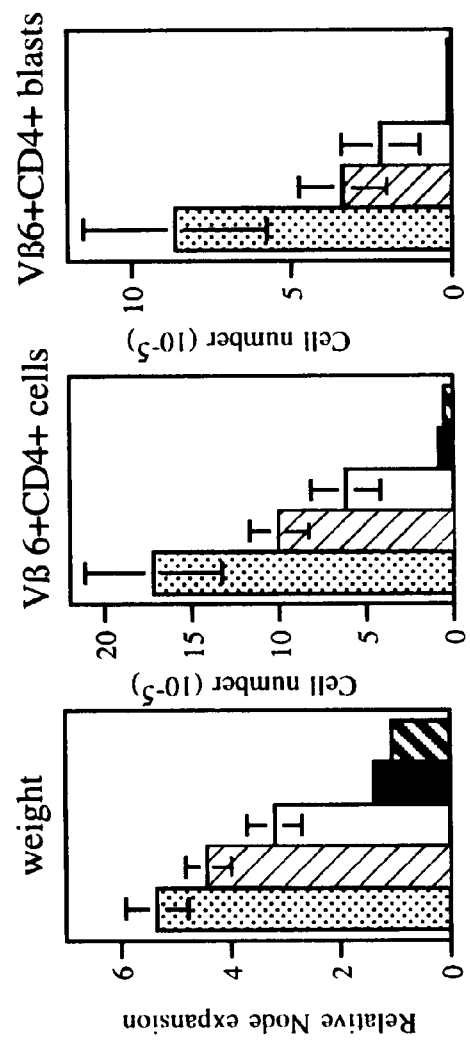
FIG. 5B is a series of bar graphs showing the effects in vivo of using MR1 alone, CTLA4Ig alone, and a combination of MR1/CTLA4Ig.

The effect of CD28 and CD40 blockade on T cell responses in vivo was assessed in C3H/HeJ (H-2$^k$, MMTV-7$^-$) immunized with DBA/2(H-2$^d$, MMTV-7$^+$) splenocytes in their foot pads. Five days after immunization the draining popliteal lymph nodes in control mice treated with human IgG demonstrated a 4–6 fold increase in weight (FIG. 5B). This was accompanied by a 30 fold expansion in the number of MMTV-7 superantigen-reactive V$\beta^+$CD$^+$4 T cells and a >90 fold increase in the number of V$\beta^+$CD$^+$T cell blasts within the popliteal lymph node. Alone, CTLA4Ig or MR1 partially inhibited these responses. In contrast, the combination of CTLA4Ig/MR1 essentially ablated the increase in lymph node size and the expansion and blastogenesis of V$\beta^+$CD4$^+$T cells (FIG. 5B).

These data show that simultaneous blockade of the CD28 and CD40 pathways inhibit complex T-dependent immune responses in vitro and in vivo.

EXAMPLE 6

This example shows that simultaneous blockade of the CD28 and CD40 pathways produces marked inhibition of both the cellular and antibody response to xenoantigen and long-term acceptance of xenogeneic (rat to mouse) cardiac and skin grafts without the need for a cytoablative conditioning therapy.

Methods

LYMPH NODE ASSAY. Male C3H (Jackson Laboratory, Bar Harbor, Me.) mice were immunized with 2×10$^6$ male Sprague-Dawley (Harlan, Indianapolis, Ind.) irradiated (2000 RADS) rat splenocytes in 50 $\mu$l of sterile normal saline in the left foot pad and 50 $\mu$l of sterile normal saline in the right foot pad and then treated intraperitoneally (i.p.) with MR1 (500 $\mu$g), CTLA4-Ig (500 $\mu$g) or both reagents (500 $\mu$g each) on days 0, 2 and 4. On day 5, the popliteal lymph nodes were removed, weighed and then teased apart, washed, before resuspension in 600 $\mu$l of RPMI 1640 with 10% FBS (Mediatech, Herndon, Va.). Each resuspended node was then divided into four equal aliquots (150 $\mu$l each). Three of the aliquots were plated into a 96 well plate. $^3$H-thymidine (1 $\mu$Ci/well) (Amersham, Arlington Heights, Ill.) incorporation was measured after 24 hours incubation at 37° C. The results for each individual animal therefore represent the mean of the 3 wells per node. The fourth aliquot was incubated for 24 hours at 37° C. and served as the source of supernatant for cytokine analysis with ELISA. Each point on all of the graphs represents the mean±standard deviation of 5 mice per group. The experiment was repeated with similar results.

CYTOKINE ELISA. Sandwich ELISA was performed using paired antibodies {anti-IL-2, anti-IFN-gamma, anti-IL-2 biotin, anti-IL-4 biotin, anti-IFN-gamma biotin (Pharmingen, San Diego, Calif.), anti IL4 (kind gift from Peter Jensen)} and streptavidin-HRP (Pierce, Rockford, Ill.). Colorimetric detection was assayed using TMB substrate (Pierce). Data were collected using a SpectraMax plate reader and plotted as absorbance (370 nm) +/– sem. Standard curves for each cytokine were generated using recombinant cytokine (rIL2, Boehringer Mannheim, Indianapolis, Ind.; rIL4, R&D Systems, Minneapolis, Minn.; and rIFN-gamma, Biosource International, Camarillo, Calif.).

MICE. Male C3H/HeJ (H-2$^k$) and DBA/2 (H-2$^d$) mice and Sprague-Dawley rats were purchased from The Jackson Laboratory (Bar Harbor, Me.) and used at 8–12 weeks of age.

CARDIAC TRANSPLANTATION. C3H/HeJ or DBA mice were transplanted with primarily vascularized Sprague-Dawley rat heart xenografts and monitored for rejection as described in Larsen C. P., Alexander D. Z., Hollenbaugh D., et al., Transplantation, 61(1):4–9 (1996) and Corry R. J., Winn H. J., Russell P. S., Transplantation, 16(4):343–350 (1973). Recipients were treated with 500 mg CTLA4-Ig combined with 500 mg MR1 on days 0, 2, 4 and 6. Control groups included recipients treated with CTLA4-Ig alone, MR1 alone or Human Ig. Paraffin embedded tissue sections (5 $\mu$m) were stained with Masson's Trichrome or hematoxylin-eosin. Histologic specimens were reviewed by a cardiac transplant pathologist (KJW) blinded to the treatment modality.

SKIN TRANSPLANTATION. Full thickness skin grafts (~1 cm$^2$) from Sprague-Dawley rats were transplanted on the dorsal thorax of C3H recipient mice and survival followed by daily visual inspection. Rejection was defined as the complete loss of visible epidermal graft tissue. Control groups included recipients treated with: CTLA4-Ig alone; MR1 alone; and Human Ig. Two additional mice in each experimental group were sacrificed at 20 days post transplant for histologic analysis.

XENOANTIBODY ASSAY. Serum was collected via tail bleed from anesthetized animals. Single cell suspensions from lymph nodes of a Sprague-Dawley rat were used as target cells, and incubated with recipient mouse serum for 20 minutes at 4° C. The cells were washed and IgG xenoantibodies were detected with donkey anti-mouse IgG Biotin (Jackson ImmunoResearch, West Grove, Pa.) followed by streptavidin-PE (Southern Biotech, Birmingham, Ala.). Cells were analyzed on a Becton-Dickinson FACscan using Cellquest Software.

Results

As an initial approach to determine the effects of CD28 and CD40 blockade on responses to xenoantigenic challenge in vivo, we used the popliteal lymph node assay as described in Larsen C. P., Elwood E. T., Alexander D. Z., et al., Nature, 381:434–438 (1996). C3H/HeJ (H-2$^k$) mice were injected with irradiated Sprague-Dawley (SD) rat splenocytes. Five days after foot pad immunization, the draining popliteal lymph nodes in control mice treated with human IgG demonstrated a 5.2 fold increase in weight relative to the contralateral node which was inoculated with sterile saline (FIG. 6A).

CTLA4-Ig partially inhibited nodal expansion. Similarly MR1 partially inhibited this response. In contrast, the combination of CTLA4-Ig/MR1 essentially ablated xenoantigen-induced lymph node expansion (FIG. 6A).

We then compared the ex vivo proliferation of lymph node cells from the different groups of xenoantigen-primed mice. While either treatment alone only partially blocked proliferation (FIG. 6B), the combination of CTLA4-Ig/MR1 essentially ablated the proliferative response (302+/−235 CPM for the combination versus 143+/−145 for a normal unstimulated node). Furthermore, the combination therapy markedly suppressed Th1 cytokines (IL-2 and IFNg) to the level of normal unstimulated cells (FIGS. 6C and 6D). Levels of the Th2 cytokine IL4 were below the level of detection in all samples.

It is important to note that this potent immune modulation is not the result of cellular deletion. Flow cytometric analysis of the peripheral blood of treated mice showed no depletion of CD4+ or CD8+ T cells, B cells, or NK cells. These data are the result of an individual analysis of 3 mice per group treated with either CTLA4-Ig or MR1 alone or the combination of these agents on days 0, 2, 4, and 6 as described in the methods section. Peripheral blood was collected by tail bleed on days 6 and 20.

Figure 7A:
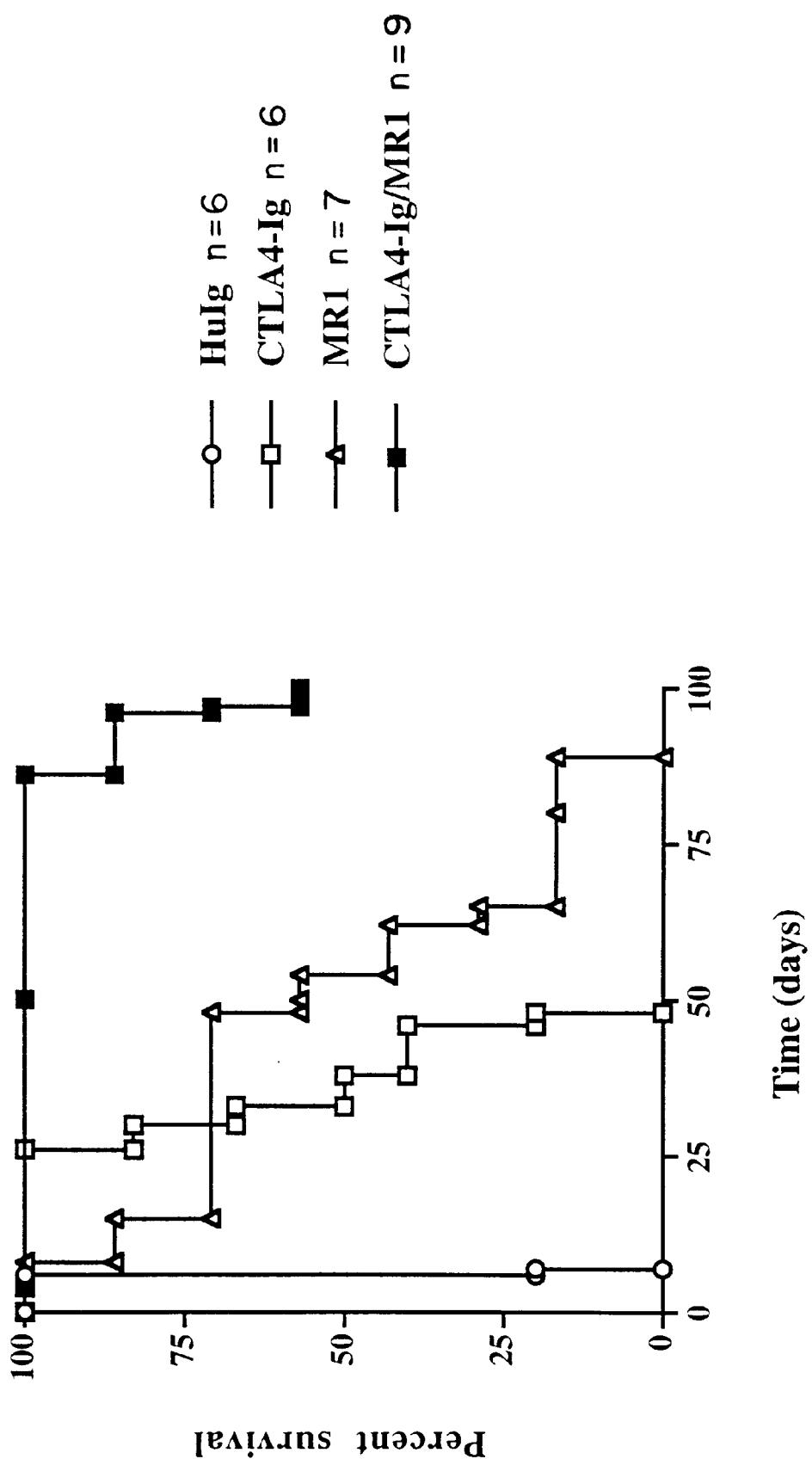
FIG. 7A is a line graph showing that C3H recipients treated with CTLA4-Ig (500 μg) on days 0, 2, 4 and 6 combined with MR1 (500 μg) on days 0, 2, 4 and 6 had prolonged survival of Sprague-Dawley rat cardiac allografts.

The results of the lymph node assays suggested that simultaneous blockade of the B7/CD28 and CD40/gp39 pathways would inhibit xenograft rejection. To explore this hypothesis we studied a vascularized cardiac xenograft model using Sprague-Dawley rats as donors and C3H/HeJ mice as recipients. Treatment with either CTLA4-Ig (MST= 33 days) or MR1 (MST=51 days) alone prolonged xenograft survival when compared to untreated controls (MST=6 days) (FIG. 7A). However, CTLA4-Ig/MR1 in combination markedly prolonged survival (MST=104.5 days).

Figure 7B:
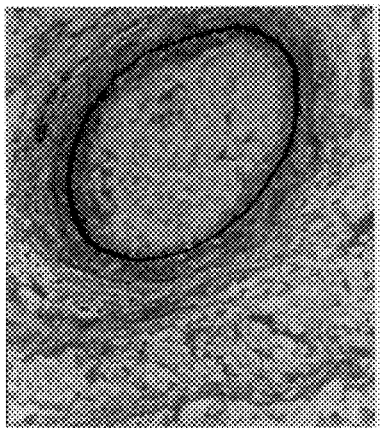
FIG. 7B is a photograph of an untreated cardiac xenograft at day 6 showing widespread tissue destruction (400X).
Figure 7C:
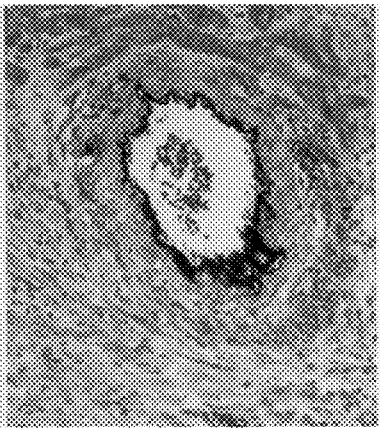
FIG. 7C is a photograph of a CTLA4-Ig treated cardiac xenograft at day 20 showing lymphocytic infiltration, myocyte destruction, and coronary vasculopathy (400X).
Figure 7D:
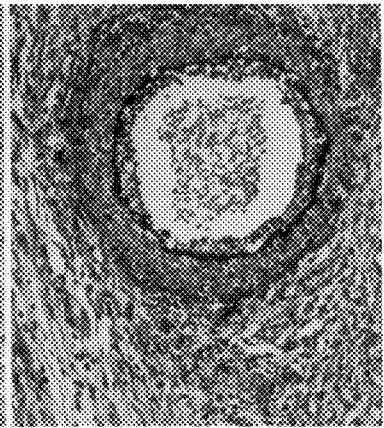
FIG. 7D is a photograph of a MR1 treated cardiac xenograft at day 20 showing lymphocytic infiltration, myocyte destruction, and coronary vasculopathy (400X).
Figure 7E:
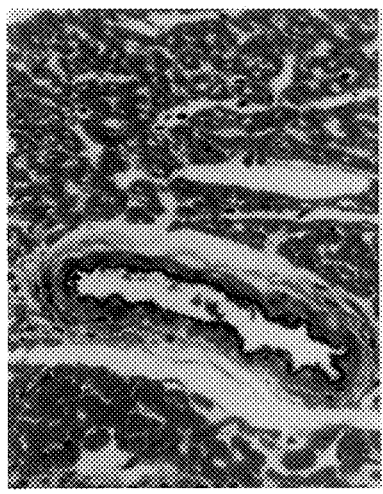
FIG. 7E is a photograph of a normal untransplanted Sprague-Dawley rat heart (400X).
Figure 7F:
FIG. 7F is a photograph of a CTLA4-Ig/MR1 treated cardiac xenograft at day 20, essentially free from lymphocytic infiltration and fibrosis (400X).
Figure 7G:
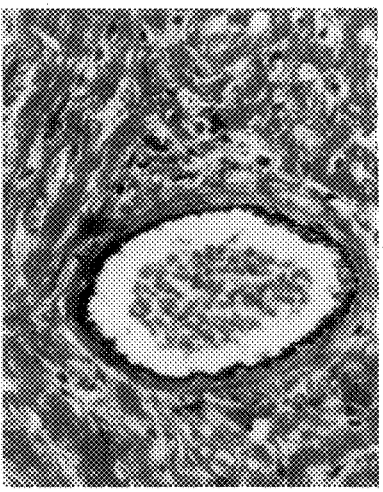
FIG. 7G is a photograph of a CTLA4-Ig/MR1 treated cardiac xenograft at day 122, demonstrating excellent preservation of both myocytes and vascular structures (400X).

When examined histologically at 20 days post-transplant, xenografts treated with either CTLA4-Ig alone (FIG. 7C) or MR1 alone (FIG. 7D) showed heavy lymphocytic infiltration with evidence of myocyte destruction and vasculopathy consistent with moderate to severe cellular rejection. In sharp contrast, the xenografts from CTLA4-Ig/MR1 treated recipients were essentially free from lymphocytic infiltration, interstitial fibrosis, and coronary arterial intimal lesions (FIG. 7F). CTLA4-Ig/MR1-treated cardiac xenografts demonstrated excellent preservation of both myocytes and vascular structures at day 122 (FIG. 7G). Untreated xenografts showed widespread tissue destruction at day 6 (FIG. 7B). A normal untransplanted Sprague-Dawley rat heart is shown in FIG. 7E.

As a more stringent test of the ability of CD40/CD28 blockade to inhibit xenogeneic immune responses, we studied the effects of short term CD28 and/or CD40 blockade, on primary skin xenograft survival in mice.

Figure 8A:
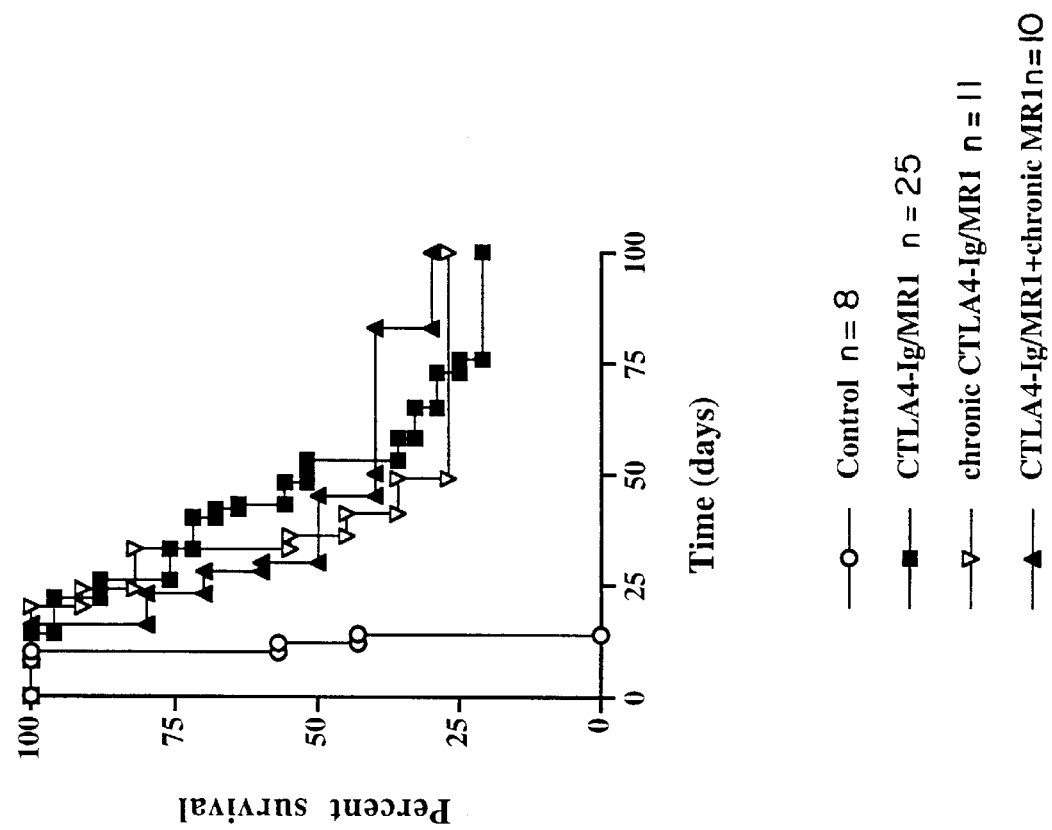
FIG. 8A is a series of line graphs showing prolongation of Sprague-Dawley rat skin xenograft survival in C3H mice treated with MR1 and CTLA4-Ig administered together in the perioperative period as compared with xenograft recipients treated with either MR1 alone or CTLA4-Ig alone and untreated controls.

C3H recipients treated with either MR1 (MST=11.5 days n=4) or CTLA4-Ig (MST=12 days n=4) alone rejected full thickness skin grafts from Sprague-Dawley rats at the same rate as untreated controls (untreated controls MST=11.5 days n=8) (FIG. 8A). In contrast, the skin xenografts on recipients treated with simultaneous MR1 and CTLA4-Ig in the perioperative period, demonstrated markedly prolonged survival (MST=53 days n=25) (FIG. 8A). A total of 25 mice received xenografts and treatment with CTLA4-Ig/MR1. With the exception of one mouse that died on day 4, all others have remained healthy throughout the experiments without signs of weight loss, infection, or malignancy.

Figure 8B:
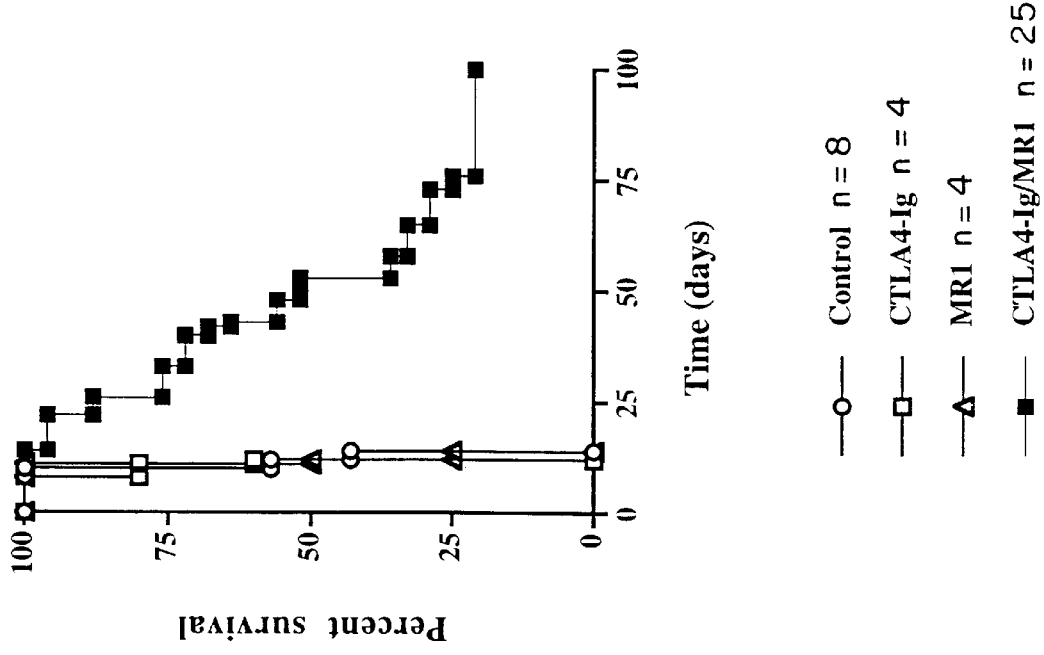
FIG. 8B is a series of line graphs showing no significant change in xenograft survival following chronic treatment (beginning after the standard 4 dose regimen) with either the CTLA4-Ig/MR1 combination or MR1.

Chronic treatment (beginning after the standard 4 dose regimen) with either the CTLA4-Ig/MR1 combination (500 µg of both agents weekly until day 100 or rejection, whichever came first) or MR1 (500 µg of MR1 weekly until day 100 or rejection) resulted in no significant change in xenograft survival (FIG. 8B).

Figure 8C:
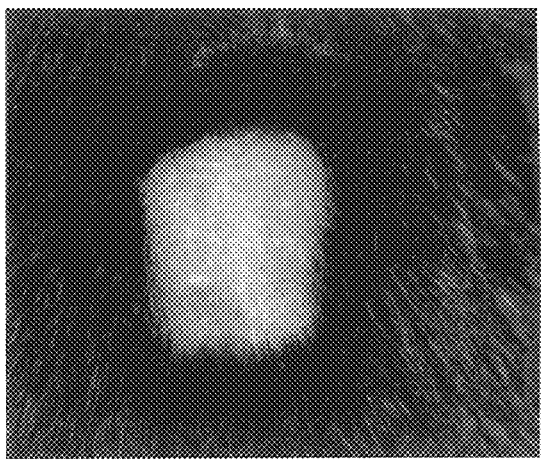
FIG. 8C is a photograph showing the healthy appearance of a Sprague-Dawley rat skin graft on a CTLA4-Ig/MR1 treated C3H recipient at 100 days after transplant.
Figure 8D:
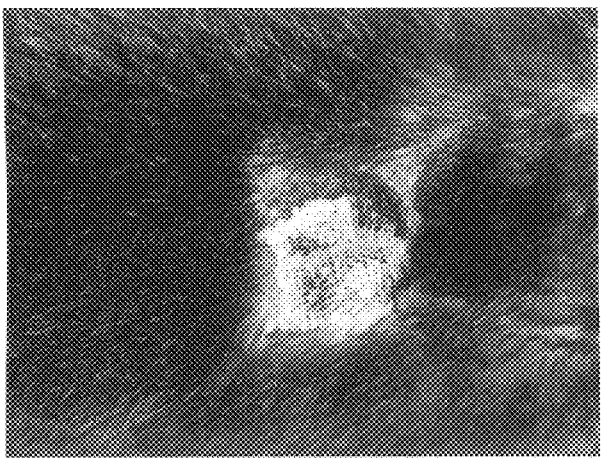
FIG. 8D is a photograph showing a control xenograft of skin undergoing rejection at 10 days post transplant.
Figure 8E:
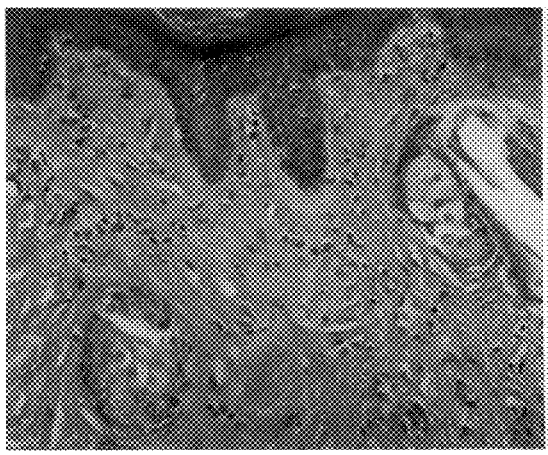
FIG. 8E is a photograph of a hematoxylin-eosin stained histologic section of an accepted CTLA4-Ig/MR1 treated graft at 50 days after transplant showing well-preserved histologic architecture (400X).
Figure 8F:
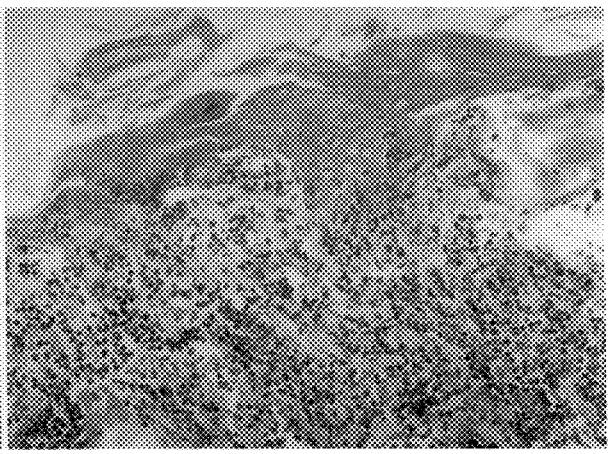
FIG. 8F is a photograph of a hematoxylin-eosin stained histologic section of a Sprague-Dawley rat skin graft on an untreated C3H recipient 8 days after transplant showing extensive lymphocytic infiltrates (400X).

Xenograft survival after simultaneous MR1/CTLA4-Ig therapy was 52% and 21% at 50 and 100 days respectively. The xenografts surviving at 50 (FIG. 8E) and 100 (FIG. 8C) days after transplantation were healthy in appearance and demonstrated well preserved histologic architecture. In untreated controls without the combination therapy, rejection was prompt and these xenografts showed marked inflammatory infiltrates (FIGS. 8D and 8F).

Similar prolongation of Sprague-Dawley skin xenografts was also observed in DBA[H-2$^d$] recipients (untreated controls MST=14 days (n=5) versus CTLA4-Ig/MR1 MST= 86 days n=5), suggesting that the potent effect of the combination treatment is not limited to a single recipient mouse strain.

The progressive loss of skin xenografts between 25 and 75 days post-transplant suggested that late graft failure might be due to subtherapeutic concentrations of CTLA4-Ig and/or MR1. To address this possibility, after the standard four-dose combination regimen mice were treated weekly with either the CTLA4-Ig/MR1 combination or MR1 alone for 100 days or until graft loss occurred. Neither of these chronic therapy strategies appreciably improved skin xenograft survival, suggesting that graft failure in CTLA4-Ig/MR1 treated mice results from factors other than inadequate drug titers and that alternate pathways not completely inhibited by CTLA4-Ig/MR1 may be important in sub-acute xenograft loss.

Figure 9A:
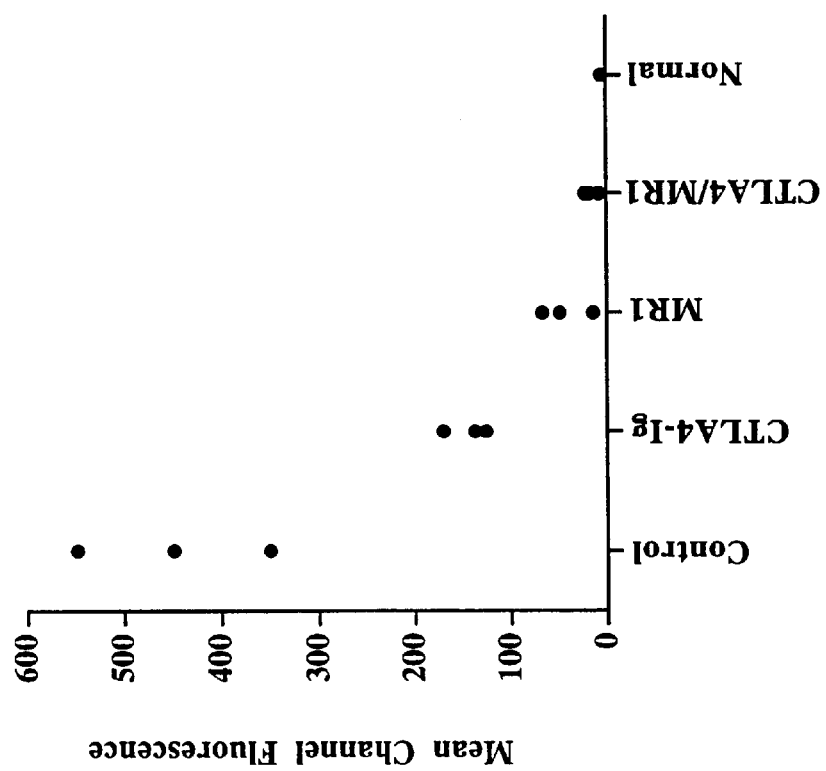
FIG. 9A is a scatter plot showing ablation of evoked xenoantibody response in serum collected from C3H recipients 55 days after skin xenografts from Sprague-Dawley donors. Control mice that had received no treatment had readily detectable IgG xenoantibody. Either CTLA4-Ig or MR1 alone partially blocked the xenoantibody response. The combination of CTLA4-Ig and MR1 essentially ablated the evoked xenoantibody response. Each data point represents the analysis of an individual recipient.
Figure 9B:
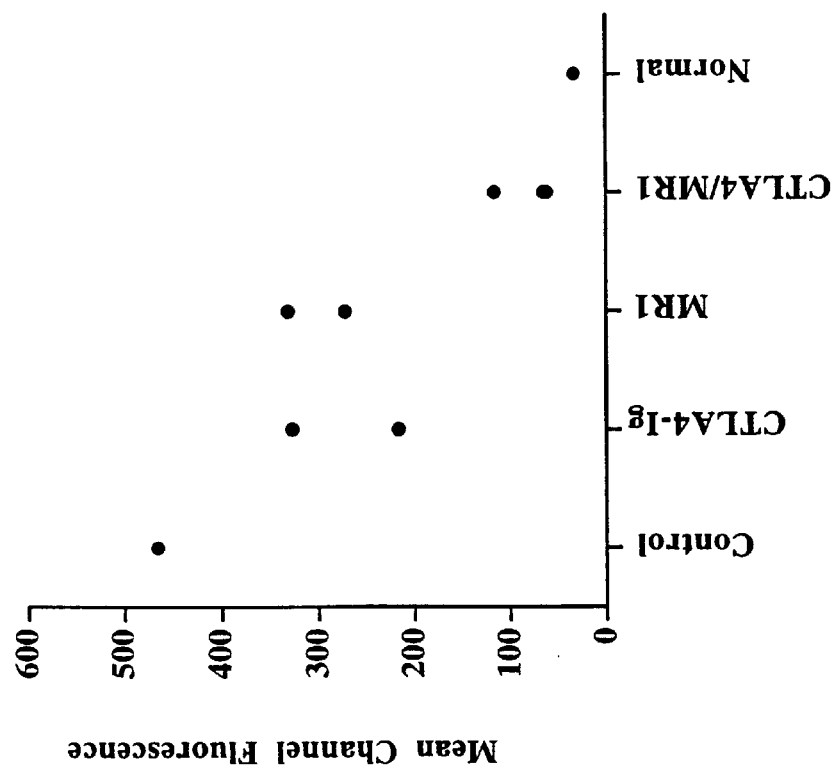
FIG. 9B is a scatter plot showing ablation of evoked xenoantibody response in serum collected from C3H recipients 20 days after heart xenografts from Sprague-Dawley donors.

In addition to cell-mediated effector mechanisms, evoked xenoantibody responses may play an important role in accelerated vascular rejection of concordant xenografts, Aksentijevich I., Sachs D. H., Sykes M., Transplantation, 53(5):1108–14 (1992). To test the effect of simultaneous blockade on evoked xenoantibody responses, serum samples from C3H/HeJ mice were analyzed for anti-rat antibodies at 55 days after receiving a Sprague-Dawley rat skin graft (FIG. 9A) and at 20 days after receiving a Sprague-Dawley rat heart graft (FIG. 9B). Treatment with either CTLA4-Ig or MR1 alone decreased the IgG antibody response, whereas the simultaneous combination CD28/CD40 blockade essentially eliminated the evoked antibody response to rat xenoantigens. Thus, inhibition of both T cell activation and antibody production could be functionally important in xenograft survival after simultaneous blockade of the B7/CD28 and CD40/gp39 pathways.

Discussion

Combined blockade of the CD28 and CD40 pathways markedly inhibits the immune response to xenoantigen. The potency of this combination therapy was particularly demonstrated in the primary skin xenograft model. Neither agent alone prolonged skin xenograft survival, while, in contrast, the simultaneous combination of CTLA4-Ig and MR1 cooperatively inhibited xenograft rejection. The uniqueness of the findings resides in the stringency of the skin graft model, as CTLA4-Ig alone has previously been shown to prolong the survival of xenogeneic pancreatic islets in a mouse model, Lenschow D., Zeng Y., Thistlethwaite J., et al., Science, 257:789–792 (1992). Long-term survival of xenogenic skin grafts have previously only been observed using vigorous cytoablative and/or hematopoeitic chimerism-based strategies, Ildstad S. T., Sachs D. H., Nature, 307:168–170 (1984), Zhao Y., Swenson K., Sergio J., Arn J. S., Sachs D. H., Sykes M., Nat. Med., 2(11):1211–1216 (1996), Mayumi H., Good R. A., J. Exp. Med., 169(1) :213–238 (1990), Cobbold S. P., Martin G., Zin S., Waldman H., Nature, 323:164–166 (1986), Qin S., Cobbold S., Benjamin R., Waldmann H., J. Exp. Med., 169:779–794 (1989).

The observation that simultaneous CD28/CD40 blockade can dramatically prolong xenograft survival suggests that both the antibody and cell mediated mechanisms for destruction of the xenograft may be effectively inhibited by this strategy. While the etiology of acute vacular xenograft rejection remains to be completely defined, there is evidence that it is caused, at least in part, by the development of xenoreactive antibodies (Cotterell A. H., Collins B. H., Parker W., Harland R. C., Platt J. L, Transplantation, 60(8):861–868 (1995)). The rapid destruction of untreated control cardiac xenografts in our model, in the absence of a cellular infiltrate, suggests a role for antibody mediated rejection. This observation and those of others (Aksentijevich I., Sachs D. H., Sykes M., Transplantation, 53(5):1108–14 (1992)), combined with the documented dramatic inhibition of the evoked xenoantibody response after blockade of the CD28 and CD40 pathways (FIGS. 9A and 9B), supports the hypothesis that xenoresponses may be sufficiently controlled by inhibition of these pathways to permit the development of non-cytoablative strategies for xenotransplantation in discordant species combinations.

While combined blockade of the CD28 and CD40 pathways markedly inhibited the xenograft rejection response, this blockade did not achieve uniform indefinite cardiac or skin graft survival in our experimental system. The observation that prolonged treatment did not improve graft survival was surprising. This suggests that inadequate blockade of these pathways is not the cause for "late" graft failure and raises the possibility that alternate pathways such as NK cells or other cells, which do not require CD28/CD40 costimulation, may promote late xenograft rejection. Suggestive evidence for the contribution of NK cells to xenograft rejection support this possibility, Zhao Y., Swenson K., Sergio J., Arn J. S., Sachs D. H., Sykes M., Nat. Med., 2(11):1211–1216 (1996), Malyguine A. M., Saadi S., Platt J. L., Dawson J. R., Transplantation, 61(1):161–164 (1996). In addition, we have shown that the inhibition of the rejection of concordant heart and skin xenografts by the simultaneous blockade of the CD40 and CD28 pathways is associated with the prevention of the "late" development of the evoked xenoreactive antibody responses (FIGS. 9A and 9B), we have not excluded the possibility that the development of an antibody response may be associated with delayed graft loss.

The ability of combined CTLA4-Ig/MR1 treatment to block the development of transplant vasculopathy in cardiac xenografts and prolong skin xenografts is of significant clinical relevance. The refinement of techniques to inhibit the effect of natural preformed xenoreactive antibodies combined with further study of CD28 and CD40 pathway blockade promises the possibility of effective new strategies to facilitate clinical xenograft transplantation.

What is claimed is:

1. A method for inhibiting transplant rejection mediated by CTLA4-positive, CD28-positive and gp39-positive cell interactions with B7-positive and CD40-positive cells in a subject comprising administering to the subject an effective amount of a combination of a first soluble ligand which prevents gp39 antigen on gp39-positive cells from binding the CD40 antigen, and a second soluble ligand which prevents B7 antigen on B7-positive cells from binding CD28 or CTLA4 thereby inhibiting transplant rejection.

2. A method for inhibiting transplant rejection mediated by CTLA4-positive, CD28-positive and gp39-positive cell interactions with B7-positive and CD40-positive cells in a subject comprising administering to the subject an effective amount of a combination of a first soluble ligand which prevents CD40 antigen on CD40-positive cells from binding the gp39 antigen and a second soluble ligand which prevents CTLA4 or CD28 on CTLA4 or CD28-positive cells, respectively, from binding B7 antigen thereby inhibiting the transplant rejection.

3. A method for inhibiting transplant rejection mediated by CTLA4-positive, CD28-positive and gp39-positive cell interactions with B7-positive and CD40-positive cells in a subject comprising administering to the subject an effective amount of a combination of a first soluble ligand which prevents gp39 on gp39-positive cells from binding the CD40 antigen and a second soluble ligand which prevents CTLA4 or CD28 on CTLA4- or CD28-positive cells from binding B7 antigen thereby inhibiting the transplant rejection.

4. A method for inhibiting transplant rejection mediated by CTLA4-positive, CD28-positive and gp39-positive cell interactions with B7-positive and CD40-positive cells in a subject comprising administering to the subject an effective amount of a combination of a first soluble ligand which prevents CD40 on CD40-positive cells from binding the gp39 antigen and a second soluble ligand which prevents B7 on B7-positive cells from binding CD28 or CTLA4 antigen thereby inhibiting the transplant rejection.

5. The method of claim 1 or 3, wherein the first soluble ligand is soluble CD40.

6. The method of claim 1 or 3, wherein the first soluble ligand is a monoclonal antibody reactive with the gp39 antigen.

7. The method of claim 6, wherein the antibody is MR1 monoclonal antibody.

8. The method of claim 1, 2, or 4, wherein the second soluble ligand is a monoclonal antibody reactive with B7 antigen.

9. The method of claim 8, wherein the antibody is anti-BB1 monoclonal antibody.

10. The method of claim 2 or 4, wherein the first soluble ligand is soluble gp39.

11. The method of claim 3, wherein the second soluble ligand is soluble B7.

12. The method of claim 2 or 4, wherein said first soluble ligand is a monoclonal antibody directed against CD40.

13. The method of claim 1 or 3, wherein said second soluble ligand is a monoclonal antibody directed against CD28.

14. The method of claim 1 or 3, wherein said second soluble ligand is a monoclonal antibody directed against CTLA4.

15. The method of claim 1, 2, or 4, wherein the second soluble ligand is soluble CTLA4.

16. The method of claim 1, 2, or 4, wherein the second soluble ligand is soluble CD28.

17. The method of claim 15, wherein the soluble CTLA4 is a recombinant binding molecule having at least a portion of the extracellular domain of CTLA4.

18. The method of claim 17, wherein the extracellular domain of CTLA4 is joined to a non-CTLA4 protein sequence.

19. The method of claim 18, wherein the non-CTLA4 protein sequence is at least a portion of an immunoglobulin molecule.

20. The method of claim 15, wherein the soluble CTLA4 is CTLA4Ig fusion protein.

21. The method of claim 15, wherein the soluble CTLA4 is a CD28Ig/CTLA4Ig fusion protein hybrid.

22. The method of claim 16, wherein the soluble CD28 is a CD28Ig/CTLA4Ig fusion protein hybrid.

23. The method of claim 20, wherein the CTLA4Ig fusion protein is CTLA4Ig designated ATCC 68629.

24. The method of claim 15, wherein the soluble CTLA4 is a CD28Ig/CTLA4Ig fusion protein hybrid having a first amino acid sequence corresponding to a portion of the extracellular domain of CD28 receptor fused to a second amino acid sequence corresponding to a portion of the extracellular domain of CTLA4 receptor and a third amino acid sequence corresponding to the hinge, CH2 and CH3 regions of human immunoglobulin Cγ1.

* * * * *

UNITED STATES PATENT AND TRADEMARK OFFICE
CERTIFICATE OF CORRECTION

PATENT NO.    : 5,916,560  
DATED         : June 29, 1999  
INVENTOR(S)   : Larsen et al.

Page 1 of 1

It is certified that error appears in the above-identified patent and that said Letters Patent is hereby corrected as shown below:

Column 1,
Line 9, the following paragraph should be inserted:

-- The invention disclosed herein was made with government support under Grant No. A13588, awarded by the National Institutes of Health. The government mary have certain rights in this invention. --.

Signed and Sealed this

Twenty-seventh Day of November, 2001

Attest:

NICHOLAS P. GODICI
*Attesting Officer*     *Acting Director of the United States Patent and Trademark Office*

UNITED STATES PATENT AND TRADEMARK OFFICE
CERTIFICATE OF CORRECTION

PATENT NO. : 5,916,560
DATED : June 29, 1999
INVENTOR(S) : Larsen et al.

It is certified that error appears in the above-identified patent and that said Letters Patent is hereby corrected as shown below:

Column 1,
Line 9, the following paragraph should be inserted:

-- The invention disclosed herein was made with government support under Grant No. AI3588, awarded by the National Institutes of Health. The government may have certain rights in this invention. --.

This certificate supersedes Certificate of Correction issued November 27, 2001.

Signed and Sealed this

Sixteenth Day of July, 2002

*Attest:*

*Attesting Officer*

JAMES E. ROGAN
*Director of the United States Patent and Trademark Office*